United States Patent
Chong et al.

(10) Patent No.: US 10,388,282 B2
(45) Date of Patent: Aug. 20, 2019

(54) MEDICAL VOICE COMMAND DEVICE

(71) Applicant: CliniCloud Inc., San Francisco, CA (US)

(72) Inventors: Hon Weng Chong, Toorak (AU); An Lin, Eight Mile Plains (AU)

(73) Assignee: CliniCloud Inc., San Francisco, CA (US)

(*) Notice: Subject to any disclaimer, the term of this patent is extended or adjusted under 35 U.S.C. 154(b) by 74 days.

(21) Appl. No.: 15/415,705

(22) Filed: Jan. 25, 2017

(65) Prior Publication Data
US 2018/0211656 A1 Jul. 26, 2018

(51) Int. Cl.
G10L 15/22 (2006.01)
G10L 17/00 (2013.01)
G10L 15/18 (2013.01)
G06F 19/00 (2018.01)
G16H 10/60 (2018.01)

(52) U.S. Cl.
CPC .......... G10L 15/22 (2013.01); G10L 15/1822 (2013.01); G10L 17/005 (2013.01); G16H 10/60 (2018.01); G10L 2015/223 (2013.01); G10L 2015/228 (2013.01)

(58) Field of Classification Search
CPC .............................. G10L 15/22; G10L 15/265
USPC ........................................................ 704/275
See application file for complete search history.

(56) References Cited

U.S. PATENT DOCUMENTS 5,832,063 A * 11/1998 Vysotsky .............. G10L 15/065
                                                    379/88.03
5,991,720 A * 11/1999 Galler ..................... G10L 15/08
                                                    704/251
2002/0046047 A1* 4/2002 Budd .................. G06F 19/3418
                                                    705/2
2006/0084847 A1* 4/2006 Reed ..................... A61B 5/0002
                                                    600/300
2006/0121904 A1* 6/2006 Reuhkala ................ H04W 8/06
                                                    455/445
2006/0190258 A1* 8/2006 Verhasselt ............. G10L 15/083
                                                    704/255
2008/0112542 A1* 5/2008 Sharma ................. H04M 3/242
                                                    379/1.02

(Continued)

FOREIGN PATENT DOCUMENTS

WO     WO-2014080252 A1 *  5/2014  ............... G01S 1/68

Primary Examiner — Paras D Shah
Assistant Examiner — Oluwadamilola M Ogunbiyi
(74) Attorney, Agent, or Firm — Lowenstein Sandler LLP

(57) ABSTRACT

Embodiments cover a voice command device and a server computing device that communicates with the voice command device. In one embodiment, a voice command device comprises a speaker, a microphone, a wireless communication module, and a processing device. The processing device is to scan for wireless advertising packets from a plurality of medical devices at an interval and detect a wireless advertising packet from a medical device of the plurality of medical devices as a result of the scanning. The processing device is further to receive medical data for a living entity from the medical device and send the medical data to a server computing device, wherein the server computing device is to generate a message associated with the medical data. The processing device is to receive the message and output the message via the speaker.

15 Claims, 12 Drawing Sheets

(56) References Cited

U.S. PATENT DOCUMENTS

| | | | | |
|---|---|---|---|---|
| 2008/0298603 A1* | 12/2008 | Smith | .................... | A61B 7/026 |
| | | | | 381/67 |
| 2008/0299970 A1* | 12/2008 | Roberts | ................ | G06Q 20/322 |
| | | | | 455/435.1 |
| 2010/0217604 A1* | 8/2010 | Baldwin | ................ | G06Q 30/02 |
| | | | | 704/275 |
| 2011/0282671 A1* | 11/2011 | Dicks | .................... | A61B 5/0022 |
| | | | | 704/270.1 |
| 2012/0143609 A1* | 6/2012 | Sannerud | ................ | G10L 17/04 |
| | | | | 704/251 |
| 2013/0238326 A1* | 9/2013 | Kim | ........................ | G06F 3/167 |
| | | | | 704/231 |
| 2014/0062694 A1* | 3/2014 | Miladin | ................ | G06F 19/325 |
| | | | | 340/539.12 |
| 2014/0122087 A1* | 5/2014 | Macho | .................... | G10L 17/22 |
| | | | | 704/275 |
| 2014/0243686 A1* | 8/2014 | Kimmel | ................ | A61B 5/1114 |
| | | | | 600/476 |
| 2015/0169284 A1* | 6/2015 | Quast | ...................... | G06F 3/167 |
| | | | | 704/275 |
| 2016/0026354 A1* | 1/2016 | McIntosh | ............... | G06Q 10/06 |
| | | | | 706/12 |
| 2016/0100276 A1* | 4/2016 | Viswanadham | ........ | H04W 4/80 |
| | | | | 455/41.2 |
| 2016/0337448 A1* | 11/2016 | Gofman | ................ | A61B 5/002 |
| 2017/0024534 A1* | 1/2017 | Arrizza | .................... | G06F 8/65 |
| 2017/0034358 A1* | 2/2017 | Bianco | ................ | H04M 7/0036 |
| 2017/0093832 A1* | 3/2017 | Schwartz | ................ | H04L 63/08 |
| 2017/0270260 A1* | 9/2017 | Shetty | ................ | A61B 5/6898 |
| 2017/0347895 A1* | 12/2017 | Wei | ...................... | A61B 5/0205 |
| 2017/0370744 A1* | 12/2017 | Miyajima | ............. | G01C 21/343 |
| 2018/0182489 A1* | 6/2018 | Harma | .................. | G06F 16/335 |
| 2018/0191726 A1* | 7/2018 | Luukkala | ............. | H04L 43/062 |

* cited by examiner

MEDICAL VOICE COMMAND DEVICE

TECHNICAL FIELD

Embodiments of the present invention relate, in general, to a voice command device that interfaces with medical devices and a backend server to manage medical data for a household.

BACKGROUND

There are multiple voice command devices that homeowners can purchase. However, current voice command devices are not designed to facilitate management of medical data.

BRIEF DESCRIPTION OF THE DRAWINGS

The embodiments described herein will be understood more fully from the detailed description given below and from the accompanying drawings, which, however, should not be taken to limit the application to the specific embodiments, but are for explanation and understanding only.

DETAILED DESCRIPTION OF THE PRESENT INVENTION

Figure 1:
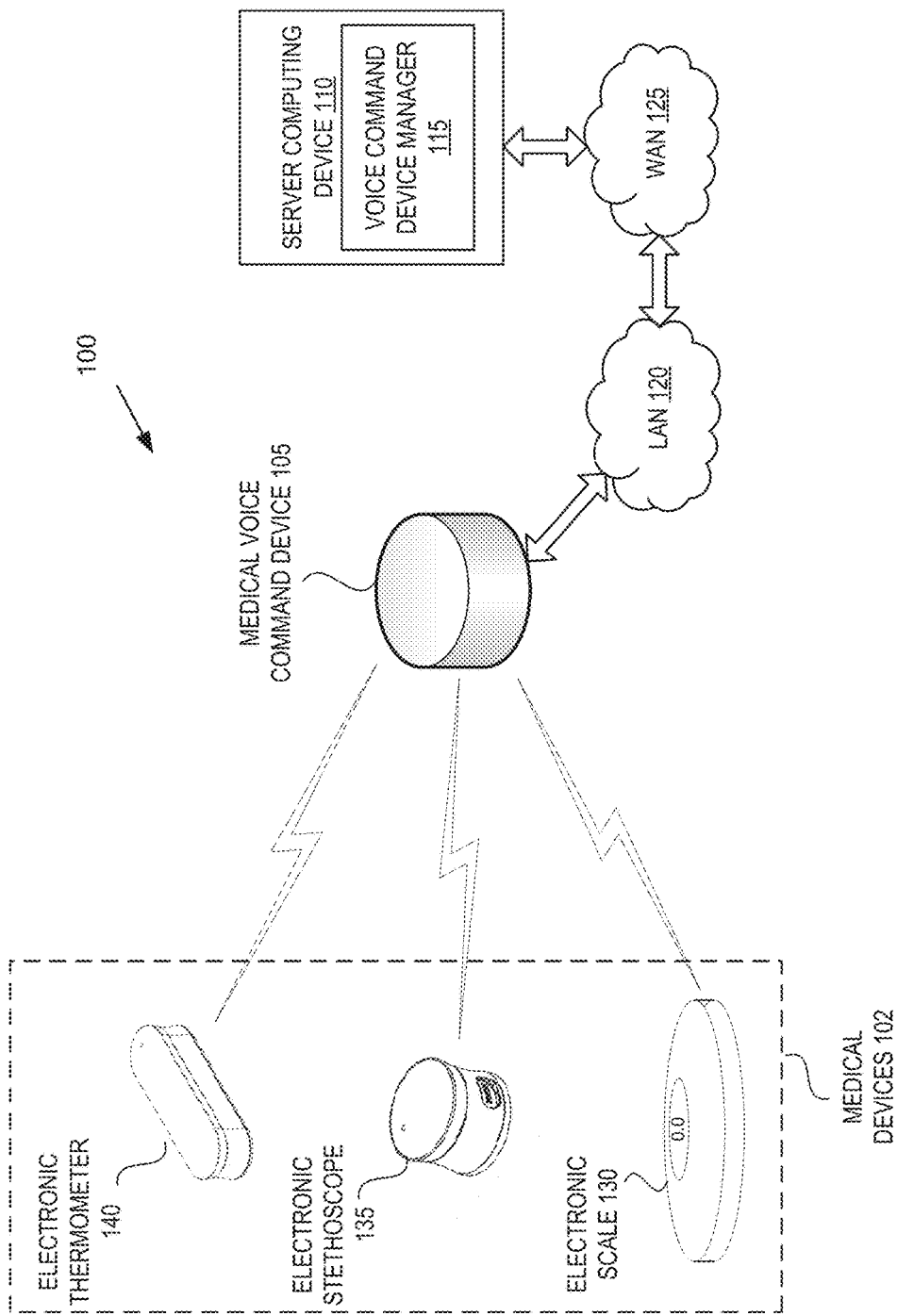
FIG. 1 illustrates an example system architecture for a medical voice command device, in accordance with one embodiment.

Described herein are embodiments of a medical voice command device and of a voice command device manager that interfaces with a medical voice command device. The medical voice command device acts as a home medical companion or medical hub that can be used to facilitate the creation of medical data (e.g., to help users take measurements regarding their health), to place prescriptions, to schedule appointments, to determine an individual's current and/or historical health, to store the medical data of multiple individuals, and/or to perform countless other tasks that relate to the health of an entire household. The medical voice command device and voice command device manager maintain multiple user accounts of different entities that are associated with the medical voice command device. The medical voice command device and voice command device manager are able to accurately determine which entity medical data is for and which user account medical data should be stored in. This provides advantages over other voice command devices that either link to only a single user account and that are unable to distinguish between multiple entities (e.g., multiple household members).

In one implementation, a medical voice command device includes a speaker, a microphone, a wireless communication module, and a processing device operatively coupled to the speaker, to the microphone, and to the wireless communication module. The medical voice command device may operate in a passive mode in which the medical voice command device receives unsolicited medical data (e.g., measurements) from medical devices. For example, the medical voice command device may scan for wireless advertising packets from a plurality of medical devices at an interval via the wireless communication module. The medical voice command device may detect a wireless advertising packet from a medical device of the plurality of medical devices as a result of the scanning, wherein the wireless advertising packet is received without first receiving a voice command. The wireless advertising packet may include medical data for a living entity. The medical voice command device sends the medical data to a server computing device, wherein the server computing device generates a message associated with the medical data. The medical voice command device receives the message and outputs (e.g., plays) a voice output of the message via the speaker.

The medical voice command device may also operate in an active mode in which the medical voice command device initiates communication with a medical device and causes the medical device to generate medical data (e.g., to take a measurement). For example, the medical voice command device may receive, via the microphone, a voice command to generate a measurement comprising medical data of a living entity (e.g., a member of a household). The medical voice command device determines a medical device that is to generate the measurement. This may include sending the voice command to a server and receiving an indication from the server of the medical device in some instances. The medical voice command device sends, via the wireless communication module, a command to the medical device to cause the medical device to generate the measurement. The medical voice command device receives, via the wireless communication module, the measurement from the medical device. The medical voice command device then sends the measurement to the server.

A server computing device may run a voice command device manager that interfaces with medical voice command devices in many households. In one implementation, the server computing device receives a voice command of a user and/or an intent and parameters of a voice command from a voice command device, wherein the voice command is a command to generate a measurement comprising medical data of a living entity. The server computing device additionally receives medical data (e.g., a measurement) associated with the voice command and determines an identity of the living entity based on the voice command and/or one or more of the intent and parameters of the voice command. The medical data may be received together with or separate from the voice command and/or parameters of the voice command. In some implementations, the medical data is included as a parameter of the voice command. The server computing device stores the medical data in a data store for a user account associated with the living entity. The server computing device additionally generates of a message such as a voice output or text output associated with the medical data and sends the message to the voice command device.

In one implementation, a server computing device receives medical data of a living entity from a voice command device, the medical data having been generated by a medical device and sent to the voice command device. The server computing device then determines an identity of the living entity and stores the medical data in a data store for a user account associated with the living entity. The server computing device initiates generation of a voice output or text output associated with the medical data and sends the voice output or text output to the voice command device.

Embodiments are described herein with reference to a medical voice command device, a server computing device that interfaces with the medical voice command device, medical data and measurements that include medical data. However, it should be understood that embodiments also apply to non-medical voice command devices that interface with devices that generate measurement data other than medical data. For example, embodiments apply to voice command devices that interface with electronic thermometers used for non-medical purposes, with digital range finders, with electronic hygrometers, with electronic rain meters, and so on. Accordingly, references made herein to medical voice command devices apply equally to other voice command devices, references made to medical data apply equally to non-medical data, and references to medical devices apply to non-medical devices with wireless connectivity.

Notably, in embodiments a medical voice command device may be associated with multiple different user accounts. These user accounts may be, for example, for the different members of a family. Embodiments provide a system that manages the medical information for the multiple different user accounts in a manner that satisfies government regulations such as the Health Insurance Portability and Accountability Act (HIPPA). Moreover, in embodiments the medical voice command device and/or server computing device are able to determine an appropriate user account of the multiple user accounts to store medical data in.

FIG. 1 illustrates an example system architecture 100 for a medical voice command device 105, in accordance with one embodiment. The medical voice command device 105 is a device that interfaces with users via voice commands to facilitate the acquisition, storage and recall of medical data. The medical voice command device 105 primarily or exclusively interfaces with users by receiving voice commands and voice responses from the users and outputting voice responses and inquiries to the users. In some implementations the medical voice command device 105 also interfaces with users by sending messages to mobile devices, computing devices, social network accounts, email addresses, etc. of the user.

The medical voice command device 105 may be placed in a household or other location, and wirelessly interfaces with one or more medical devices 102 in the household or other location. Each of the medical devices 102 that interfaces with the medical voice command device 105 is preferably within a wireless communication range of the medical voice command device 105. Examples of medical devices 102 include an electronic thermometer 140, an electronic stethoscope 135 and an electronic scale 130. Other types of medical devices 102 that may interface with the medical voice command device 105 include an electronic blood pressure monitor, an electronic glucose level monitor, an electronic oximeter, an electrocardiograph machine, an electronic blood alcohol level sensor, a pacemaker, an activity tracker (e.g., such as a FitBit®, Jawbone UP®, Garmin Vivofit®, Nike Fuelband®, Microsoft Band®, etc.), a medical alert watch, a heartrate monitor, and so on. Medical voice command device 105 may interface with any medical devices 102 that have wireless communication capabilities.

Medical voice command device 105 may support one or multiple different wireless communication standards. In one implementation, medical voice command device 105 supports Wi-Fi® and Bluetooth®. Medical voice command device 105 may additionally or alternatively support other wireless communication protocols such as Zigbee, Z-Wave, 6LoWPAN, Bluetooth Low Energy (BLE), Thread, near field communication (NFC), radio frequency identifier (RFID), and/or other wireless communication protocols.

Medical voice command device 105 may include an active mode in which the medical voice command device 105 initiates measurements for one or more medical devices 102. The active mode may be performed after a user issues a verbal instruction called a voice activation command that causes the medical voice command device 105 to transfer out of a low power state. The voice activation command may be a specific phrase that a user speaks to activate the medical voice command device, such as "Hey CC."

Medical voice command device 105 may receive a voice activation command, and may transfer out of the low power state. The medical voice command device 105 may then receive a voice command to take a measurement, such as a command to "take Johnny's temperature" or to "measure my weight." Responsive to receiving a voice command to take a measurement (or otherwise to generate medical data), medical voice command device 105 may determine an intent of the command (e.g. a type of measurement to generate), and then determine an appropriate medical device 102 that is capable of generating the requested measurement. Once the medical device is determined, medical voice command device 115 may send a command to that medical device 102.

In an example, responsive to a request to "take Johnny's temperature," medical voice command device 105 may determine that electronic thermometer 140 is in range of the medical voice command device 105, is activated, and is capable of generating a temperature measurement. Medical voice command device 105 may then send a command to electronic thermometer 140 that causes electronic thermometer 140 to generate a temperature measurement. Medical voice command device 105 may additionally output voice instructions for a user to place the electronic thermometer 140 near Johnny's temple (or to otherwise prepare the electronic thermometer 140 for generation of the temperature measurement). The electronic thermometer 140 may then generate the temperature measurement and send the temperature measurement to medical voice command device 105.

Medical voice command device 105 may additionally include a passive mode in which the medical voice command device 105 continually or periodically scans for unsolicited wireless messages (e.g., packets) from medical devices 102. The passive mode may be a low power mode in which most of the components of the medical voice command device 105 are unpowered or are in a low power consumption state. The wireless packets may be, for example, wireless advertising packets from medical devices 102 (e.g., Bluetooth, Wi-Fi or BLE advertising packets).

A user may interface directly with a medical device 102 to produce a measurement (e.g., to produce medical data). The medical device 102 may then generate an unsolicited wireless message (e.g., a wireless advertising packet) that includes the measurement, and may broadcast the unsolicited wireless message using a wireless communication protocol. The medical voice command device 105 may detect and receive the unsolicited wireless message (which may include a measurement) as a result of scanning for unsolicited messages.

In an example, a member of a household may step onto electronic scale 130. Electronic scale 130 may generate a weight measurement, and may then generate a wireless advertising packet and insert the weight measurement into the wireless advertising packet. Electronic scale 130 may broadcast the wireless advertising packet, which may be detected and received by medical voice command device 105.

Some medical devices 102 require pairing. For such a medical device 102, medical voice command device 105 may initially pair with the medical device 102 with user input. For example, a user may initiate Bluetooth pairing by pressing a button on a medical device 102 and issuing a voice command to medical voice command device 105 to "pair with the medical device 102." The voice command may specify the medical device 102 to pair with generically (e.g., by simply asking to initiate pairing without specifying which device is to be paired with). Alternatively, the voice command may specify the medical device with specificity (e.g., by identifying one or more of the type of medical device, the brand of medical device, the model of medical device, and so on). Pairing may be performed using the standard pairing mechanism for the wireless communication protocol that is used to connect to the medical device 102 that is being paired to the medical voice command device 105.

Once the medical voice command device 105 is paired with a medical device 102, the medical voice command device 105 may scan for unsolicited wireless messages from the medical device 102, where the unsolicited wireless messages may include a request to connect to the medical device 102. Additionally, or alternatively, the medical voice command device 105 may issue connection requests to the medical device 102 that is paired with the medical voice command device 105. Once a connection is established between the medical voice command device 105 and the medical device 102, the medical device 102 may send measurement data (e.g., medical data) to the voice command device and/or the voice command device 105 may send commands to generate measurement data to the medical device 102.

In addition to interfacing with medical devices 102, medical voice command device 105 additionally interfaces with a server computing device 110 that is usually not located in the household or other location of the medical voice command device 105. The server computing device 110 may be a physical server computing device or a virtual server that runs on underlying physical hardware. For example, the server computing device 110 may run in a cloud environment such as Amazon's® Elastic Compute Cloud (EC2®). Medical voice command device 105 may be connected to a local area network (LAN) 120 at the household or other location. The medical voice command device 105 may be connected to the LAN via a wired connection (e.g., an Ethernet connection) or a wireless connection (e.g., a Wi-Fi connection). The LAN 120 may be connected to a wide area network (WAN) 125 such as the Internet or an intranet, and the server computing device 110 may likewise be connected to the WAN 125.

Server computing device 110 includes a voice command device manager 115 that interfaces with, and supports the functionality of, medical voice command device 105. When medical voice command device 105 receives medical data (e.g., measurements), it may send that medical data to the voice command device manager 115. The voice command device manager 115 may then determine an identity of a living entity (e.g., a household member) for whom the medical data was generated, and may store the medical data for that living entity in a medical data store in association with a user account of that living entity. Additionally, when medical voice command device 105 receives voice commands, the medical voice command device 105 may send those voice commands (or an intent and parameters determined from the voice commands) to voice command device manager 115. The voice command device manager 115 may perform voice recognition to parse the voice command if a voice command is received. The voice command device manager 115 may send instructions back to the medical voice command device 105 based on the parsed voice command and/or based on the received intent and parameters of the voice command. Medical voice command device manager 115 may additionally generate messages such as voice outputs and/or text outputs that notify a user of the received medical data (e.g., a received temperature, heart-rate, etc.) and/or of additional information associated with that medical data. For example, if a temperature is above a threshold (e.g., above 100 degrees Fahrenheit), then the voice output or text output may state that the entity whose temperature was taken has a fever and may recommend over the counter medication. If the temperature is above a higher threshold (e.g., above 104 degrees Fahrenheit), then the voice output or text output may recommend immediate medical attention by a doctor and/or may offer to call 911 on behalf of the entity. If a text output is generated, then the medical voice command device 105 may process the text output to convert the text output into a voice output. The voice command device manager 115 additionally performs numerous other functions, which are discussed in greater detail below.

Figure 2:
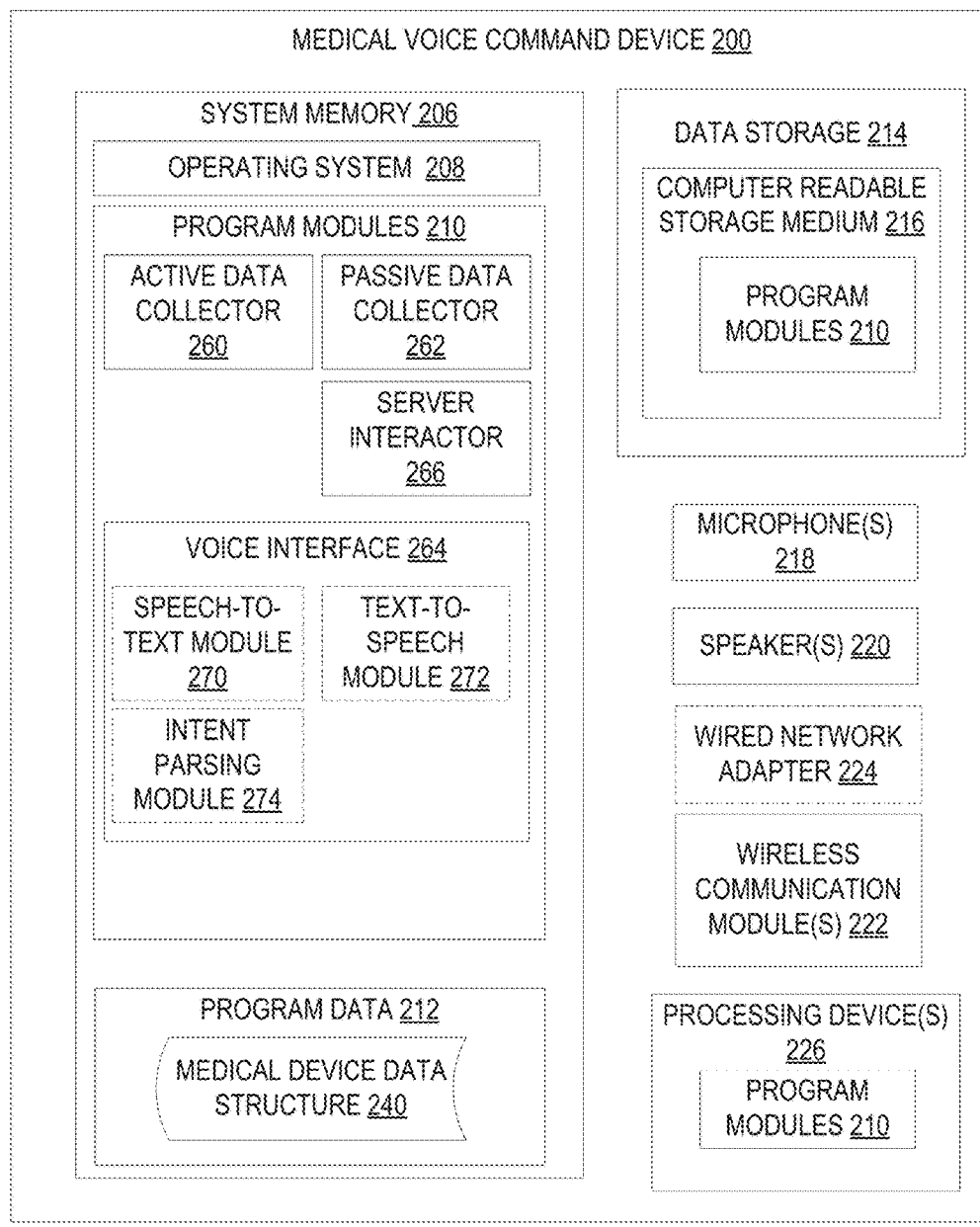
FIG. 2 is a block diagram illustrating one embodiment of a medical voice command device.

FIG. 2 is a block diagram illustrating one embodiment of a medical voice command device 200. The medical voice command device 200 may be a home medical hub, and may correspond to medical voice command device 105 of FIG. 1.

The medical voice command device 200 includes one or more processing devices 226, such as one or more central processing units (CPUs), microcontrollers, field programmable gate arrays (FPGAs), digital signal processors (DSPs), and/or other types of processors. The medical voice command device 200 also includes system memory 206, which may correspond to any combination of volatile and/or non-volatile storage mechanisms. The system memory 206 stores information which provides an operating system component 208, and various program modules 210 such as active data collector 260, passive data collector 262, voice interface 264 and server interactor 266. The medical voice command device 200 performs functions by using the processing device(s) 230 to execute instructions provided by the system memory 206. Alternatively, the program modules 210 may be implemented in firmware, hardware, or a combination of software, firmware and/or hardware.

The medical voice command device 200 also includes a data storage device 214 that may be composed of one or more types of removable storage and/or one or more types of non-removable storage. The data storage device 214 includes a non-transitory computer-readable storage medium 216 on which is stored one or more sets of instructions embodying any one or more of the methodologies or functions described herein. As shown, instructions for one or more of the program modules 210 may reside, completely or at least partially, within the computer readable storage medium 216, system memory 206 and/or within the processing device(s) 226 during execution thereof by the medical voice command device 200, the system memory 206 and the processing device(s) 226 also constituting computer-readable media.

The medical voice command device 200 includes one or more microphones 218 (e.g., a microphone array) that act as the input devices for the medical voice command device 200. The medical voice command device 200 additionally includes one or more speakers (e.g., an array of speakers) that act as the output devices for the medical voice command device 200. While the medical voice command device may additionally include other input devices (e.g., (e.g., keyboard, mouse device, touchpad, touchscreen, specialized selection keys, etc.) and/or output devices (e.g., displays, printers, tactile feedback mechanisms (e.g., vibrators), etc.), the primary user interface with the voice command device 200 is envisioned to be a voice interface via the microphones 218 and speakers 220.

The medical voice command device 200 further includes one or more wireless communication modules 222, such as a Bluetooth module, a Zigbee module, a Wi-Fi module, and so forth. The wireless communication modules 222 may additionally or alternatively include a wireless modem to allow the medical voice command device 200 to communicate via a wireless network provided by a wireless carrier. The wireless modem may be configured to communicate using wireless communication standards and protocols such as global system for mobile communications (GSM), code division multiple access (CDMA), wideband code division multiple access (WCDMA), time division multiple access (TDMA), universal mobile telecommunications system (UMTS), long term evolution (LTE), worldwide interoperability for microwave access (WiMAX), and so on.

In one embodiment, the medical voice command device 200 includes a Bluetooth wireless communication module to interface with medical devices via Bluetooth and a Wi-Fi wireless communication module to wirelessly connect to a LAN. The medical voice command device 200 may additionally include a wired network adapter 224 such as an Ethernet adapter in some implementations. Other combinations of wireless communication modules 222 and/or a wired network adapter 224 may also be used.

The active data collector 260, passive data collector 262, voice interface 264 and/or server interactor 266 may be modules of a voice command device program that runs on the processing device 226. Alternatively, one or more of the active data collector 260, passive data collector 262, voice interface 264 and/or server interactor 266 may be separate programs that execute on the processing device 226. The program modules 210 may be programmed to execute on the iOS® operating system, the Android® operating system, the Windows® operating system, a Linux® operating system, or another operating system.

Voice interface 264 may be responsible for interpreting voice commands received via the microphones and outputting voice responses and other voice outputs via speakers 220. System memory 206 may include program data 212 that may include a set of supported voice commands. When a new voice command is received, voice interface 264 may compare the received voice command to the set of recognized voice commands to identify the voice command. If the received voice command varies from one of the included voice commands by less than a threshold, then voice interface 264 may identify the received voice command as corresponding to the matching supported voice command. If the received voice command does not match a supported voice command in the set of supported voice commands, then server interactor 266 may forward the voice command to a server computing device for further processing. The server interactor 266 may then receive instructions based on the voice command (which may have been parsed and recognized by the server computing device) and/or may receive a voice output for voice interface 264 to play via speakers 220. Alternatively, in some implementations all voice commands are forwarded by server interactor 266 for processing.

TABLE 1

Example operations and associated voice commands

| Operation | Example Voice Commands | Possible outcomes |
| --- | --- | --- |
| Take measurement | Take my temperature, Take Toby's Temperature | "Temperature is XX.X degrees Fahrenheit", "The temperature is normal", "The temperature has gone up from 2 hours ago", "It looks like [Toby] has a fever, do you want me set a reminder for Tylenol?", "It look like [Toby]'s temperature remains high, do you want me to contact a physician?" |
| Manual data input | "My temperature is 37.4 degrees.", "Today my weight is 121 pounds" | Same as smart device input. "I made a mistake" to delete a user input data within last 5 minutes |
| Correct user input mistake | "I made a mistake", "I made an error" | |
| Search database | "What was Toby's last temperature recordings?", "What was Toby's average temperature in the last 2 days?", "How often has Toby had a fever | Time, date, frequency, value as applicable |

TABLE 1-continued

Example operations and associated voice commands

| Operation | Example Voice Commands | Possible outcomes |
| --- | --- | --- |
| | in the last year?", same with other recording types, like BP, Heart Rate | |
| Sending to doctor | "Send my BP readings from last month to my physician", "Share my heart recording with Dr. Chong" | "Recordings have been sent" |
| Set medication reminders | "Remind me to give Tylenol 3 times a day for the next 2 days" | "Reminders have been set in the next 3 days, for 8am, 2pm and 7pm." [Hub and phone app both get push notifications] |
| Closest pharmacy | "Where is my closest pharmacy", "How much is [drug]", "Where can I get Ventolin nearby?" | "The cheapest within 5 miles is at Walgreens on Broadway for $12.95, but the closest is Rite-aid for $15.34. It will be open until 9pm." |

One example set of supported voice commands and associated operations is set forth in the table above. The table identifies example voice commands that trigger particular operations and possible outcomes of those operations.

In one embodiment, voice interface 264 includes a speech-to-text module 270. The speech-to-text module 270 may perform automated transcription of a voice command or other voice input to transform the voice command into a text command. In one embodiment, the speech-to-text module 270 includes an application programming interface (API) to call a third party voice recognition service such as Siri®, Cortana®, Google Now®, and so on. In such an implementation, speech-to-text module 270 sends an audio file to the third party voice recognition service, and receives a text version of the voice command.

In one embodiment, voice interface 274 further includes an intent parsing module 274. The intent parsing module 274 parses the text version of the voice command to determine an intent of the voice command and one or more parameters of the voice command. The intent parsing module 274 may determine, for example, a requested action to perform (e.g., take temperature), an object to perform the action on (e.g., Johnny's temperature), a time to perform the action, and so on. This may include determining which supported operation (e.g., from Table 1 above) is being requested. In one embodiment, the intent parsing module 274 includes an API for a third party intent parsing service such as Microsoft's Language Understanding Intelligent Service (LUIS).

Various supported voice commands may be associated with one or more operations to be performed by the medical voice command device and/or by the remote server computing device. One example supported voice command is a command to generate medical data and/or to take a measurement associated with medical data. For example, a received voice command may be to "take my temperature." If a "take measurement" command is identified, medical voice command device and/or the server computing device determines a medical device that will generate the measurement.

In one embodiment, medical voice command device includes a list, table or other data structure (referred to herein as the medical device data structure 240) that indicates each of the medical devices that are associated with the medical voice command device (e.g., that are in a same household as the medical voice command device and/or that are owned by a user of the medical voice command device). The medical device data structure 240 may indicate the types of measurements that each of the listed medical devices is capable of producing.

In one embodiment, the medical voice command device comes pre-populated with information on the most popular medical devices. A user may indicate to the medical voice command device which medical devices that user owns, and the indicated medical devices may be added to the medical device data structure. If medical devices are indicated for which the medical voice command device does not include preloaded information, then the medical voice command device may query the server computing device for information on these devices.

Responsive to a command to take a measurement, the server computing device and/or voice interface 264 (e.g., the intent parsing module 274 of the voice interface 264) determine the type of measurement to be taken. The voice interface 264 and/or server computing device additionally determine (e.g., by comparing the determined measurement to the medical device data structure 240) the medical device to generate the measurement.

Medical device data structure 240 may additionally include information usable to communicate with each of the medical devices. This may include an indication of a wireless communication protocol to use for communication with a medical device, a media access control (MAC) address of the medical device, a unique identifier of the medical device, a security key to use for communications with the medical device, and so on. Active data collector 260 may use the information from the medical device data structure 240 to communicate with the medical device via an appropriate wireless communication module. This may include sending a command to the medical device to cause the medical device to generate the measurement. Active data collector 260 may then receive the measurement and/or other medical data from the medical device. Server interactor 266 may send the measurement/medical data to the server computing device via the wired network adapter 224 or an appropriate wireless communication module 222.

Medical voice command device 200 may default to a low power state. While the medical voice command device 200 is in the low power state, it may listen for two types of input. The first type of input is unsolicited wireless messages from medical devices. The second type of input is a voice activation command from a user. Responsive to detecting either type of input, medical voice command device 200 transitions out of the low power state and into a fully powered state.

While the medical voice command device is in the low power state, passive data collector 262 may periodically or continuously scan for unsolicited wireless messages (e.g., wireless advertising packets) from medical devices. Passive data collector 262 may use the medical device data structure 240 to determine which devices might send unsolicited messages. The medical device data structure 240 may indicate what communication protocol such medical devices use, what ports they might send information on, and/or other information that is usable to determine how passive data collector 262 is to scan for unsolicited messages. Passive data collector in one embodiment scans the appropriate frequencies for unsolicited messages (e.g., the appropriate protocols). Responsive to receipt of an unsolicited message that includes medical data (e.g., a measurement), medical voice command device 200 powers on and server interactor 268 forwards that medical data on to the server computing device.

When medical data, a voice command and/or an intent and properties from a voice command are sent by server interactor 266 to the server computing device, the server computing device attempts to identify an entity associated with the medical data and/or voice command. If the server computing device is unable to determine the identity with the information that it presently has, then it generates an inquiry and sends that inquiry to medical voice command device. The inquiry may be a voice inquiry or a text inquiry. Voice interface 264 may then play the voice inquiry (e.g., an inquiry asking who the medical data is for), and receives a voice response. In one embodiment, voice interface 264 includes a text-to-speech module 272. The text-to-speech module 272 may include an API that calls a third party text-to-speech service. If the received inquiry is a text inquiry, then text-to-speech module 272 may process the text inquiry to convert it into a voice inquiry. Voice interface 264 may then play the voice inquiry using speakers 220. Server interactor 266 then sends the voice response to the server computing device to provide the server computing device with additional information to identify the entity to associate with the medical data (e.g., the patient or living entity for which a medical measurement was generated). The intent and/or parameters of the voice response may be determined by processing the voice response using speech-to-text module 270 to generate a text response and then subsequently processing the text response using intent parsing module 274.

Figure 3:
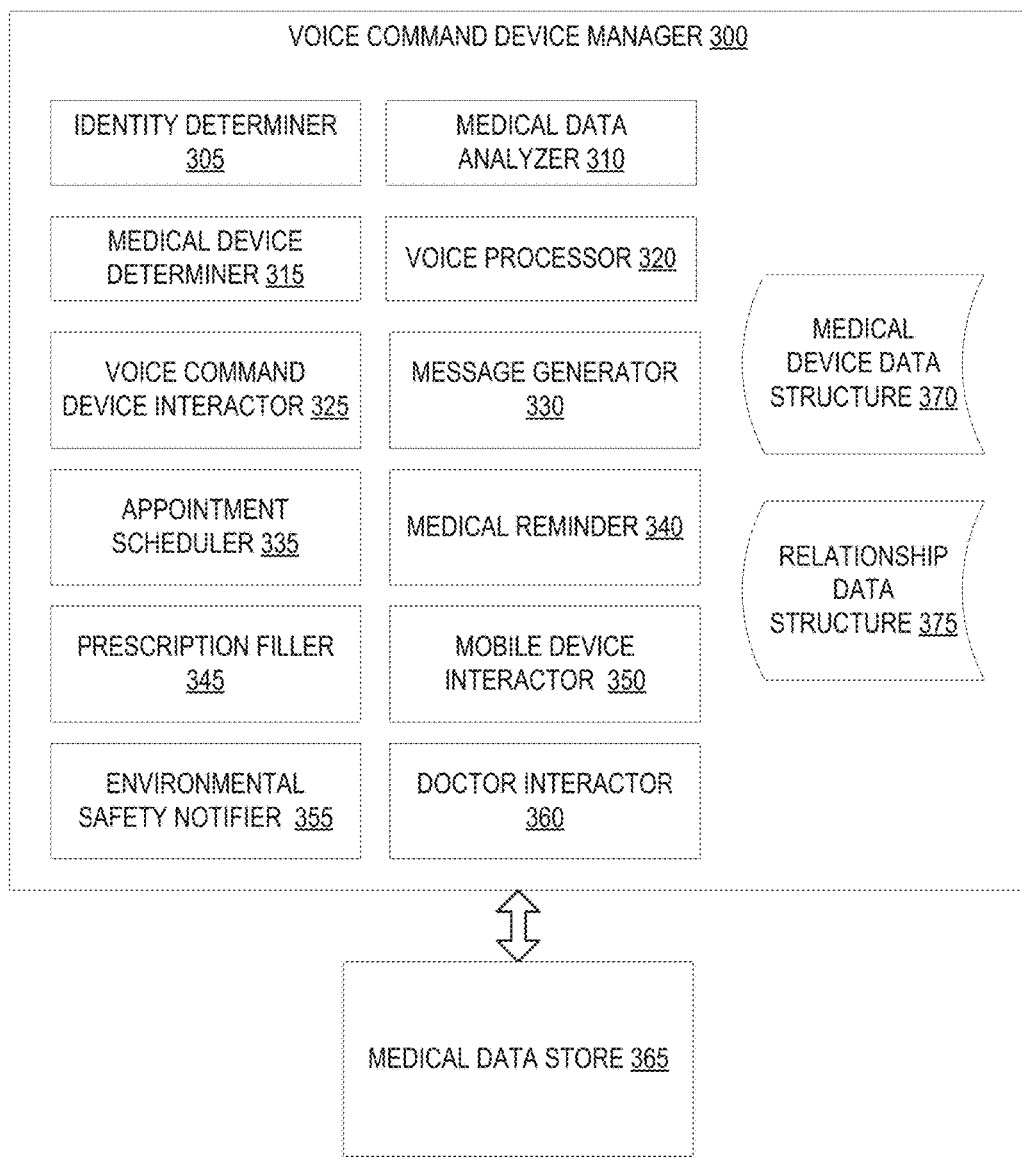
FIG. 3 is a block diagram of a voice command device manager that runs on a server computing device, in accordance with one embodiment.

FIG. 3 is a block diagram of a voice command device manager 300 that runs on a server computing device, in accordance with one embodiment. Voice command device manager 300 may execute, for example, on server computing device 110 of FIG. 1. In one embodiment, the voice command device manager 300 includes a voice command device interactor 325, an identity determiner 305, a medical data analyzer 310, a voice processor 320 and/or a message generator 330. Voice command device manager 300 may additionally or alternatively include an appointment scheduler 335, a medical reminder 340, a prescription filler 345, a mobile device interactor 350, an environmental safety notifier 355 and a doctor interactor 360. The functionality of any one or more of these components may be combined into a single module or may be divided into multiple modules.

Voice command device interactor 325 receives voice commands, information on intent and/or properties of voice commands (e.g., files such as JSON files that include a determined intent and properties associated with a voice command), medical data (e.g., measurements), and/or other data from medical voice command devices. Received voice commands may include voice activation commands, voice commands to generate measurements, voice inquiries asking for medical information, voice commands to schedule doctor appointments, voice commands to fill prescriptions, and so on.

After voice command device interactor 325 receives a voice command from a voice command device, voice processor 320 may process the voice command to determine contents of the voice command. For example, voice processor 320 may perform voice recognition to determine a nature of the voice command and/or to transcribe the voice command into a text command. In one embodiment, voice processor 320 uses a third party voice recognition service to perform the voice recognition. Examples of third party voice recognition services include Microsoft's Cortana®, Google's Google Now®, and Apple's Siri®.

Once the content of the voice command is determined by voice processor and/or the voice command is converted to a text command, voice processor 320 may compare the text command to a finite set of supported commands to determine which command most closely matches the text command. In one embodiment, voice processor 320 includes an intent parsing module (not shown) that determines an intent of the text command and/or parameters of the text command as described with reference to intent parsing module 274 of FIG. 2. If the command relates to the use of a medical device (e.g., taking a measurement using a medical device), then medical device determiner 315 may determine an appropriate medical device to satisfy the command. Alternatively, or additionally, the processing of the voice command and the determination of a medical device to use for satisfying the voice command may be determined by a medical voice command device that received the voice command. In such an embodiment, a file including an identified intent of the voice command and determined parameters of an voice command may be received by voice command device manager 300.

Some voice commands may be voice instructions to record particular measurements. For example, a user may include a non-connected medical device (e.g., a medical device that does not have wireless communication capability). In such an instance, the user may take a measurement using the medical device, and may issue a voice command to record the measurement.

In one embodiment, voice command device manager 300 includes a medical device data structure 370 that is associated with one or more user accounts associated with a particular household. The medical device data structure 370 may be a list, table, database, or other data structure that includes an identity of one or more medical voice command devices used for the one or more user accounts as well as the medical devices that are associated with those one or more user accounts.

A voice command may specify a particular type of measurement to be generated (e.g., a temperature measurement). The medical device data structure 370 may associate each medical device entry with one or more types of measurements. Medical device determiner 315 may compare the determined type of measurement to the entries in the medical device data structure 370 to determine a medical device that will be used to generate a measurement.

Once a medical device is determined, voice command device interactor 325 may notify the medical voice command device of the medical device to use to generate the measurement. Voice command device interactor 325 may additionally or alternatively generate an instruction that will cause the voice command device to send a command to the determined medical device. The command may cause the medical device to generate the requested measurement and send that measurement back to the medical voice command device. The medical voice command device will then return the measurement back to voice command device interactor 325.

Medical devices may also generate measurements/medical data independently (e.g., based on a user interacting with the medical devices) and send the measurements/medical data to the voice command device. The medical voice command device may then send the measurements/medical data to voice command device manager 300.

A single voice command device will typically be associated with multiple different user accounts and/or with multiple different entities. For example, a single household may include a mother, a father, and one or more children. Each member of the household may have a separate user account that is associated with the voice command device. Accordingly, when a measurement or other medical data is generated, identity determiner 305 determines who the measurement was for. Identity determiner 305 determines the identity of an entity (a living entity such as a household member, patient, or other living entity) for whom a measurement/medical data was generated, as well as a user account of that entity. Identity determiner may use one or more heuristics and/or identity identification rules to determine the identity of the entity.

If a measurement was initiated by a medical voice command device responsive to a voice command from a user, then the voice command may have been preceded by a voice activation command. Additionally, the voice command may have specified the identity of the entity using a name, a possessive pronoun or a possessive adjective.

A voice activation command is a particular phrase that a user speaks to activate a medical voice command device. Voice command device manager 300 and/or the medical voice command device itself may include multiple voice activation command recordings, where each voice activation command recording is associated with a particular entity (e.g., with a particular user account). Identity determiner 305 may perform voice print identification by comparing a received voice activation command to voice activation commands stored in a data store that are associated with a particular voice command device from which the voice activation command was received. Identity determiner 305 may determine that the speaker of the voice activation command corresponds to the user account having the recorded voice activation command that most closely matches the received voice activation command.

In one embodiment, voice command device manager includes a table, tree, web, database, or other relationship data structure 375 that identifies the relationships between the different user accounts associated with a medical voice command device. The relationship data structure 375 may indicate the type of relationship between each user account. For example, if a household includes a mom, a dad, a son, and a daughter, then the relationship data structure may link the dad to the mom by a husband-wife relationship, may link the dad to the son by a father-son relationship, and may link the dad to the daughter by a father-daughter relationship.

Once the speaker of the voice command is known, identity determiner 305 may determine a relationship between the speaker and the entity if a possessive pronoun or possessive adjective was used in the voice command. In one embodiment, the relationship is determined using the relationship data structure 375. For example, identity determiner 305 may determine aa first entry in the relationship data structure that corresponds to the speaker based on the previously determined identity of the user. Identity determiner 305 may then determine a second entry in the relationship data structure based on the possessive pronoun or the possessive adjective in the voice command, wherein the second entry indicates the identity of the living entity. For example, if the voice command was "take my daughter's temperature," and the speaker was the father in the previous example, then the possessive adjective "my" followed by "daughter" would be compared to the relationship data structure 375 to determine the user account that has the father-daughter relationship with the speaker.

In a simpler example, a speaker may use a possessive pronoun or possessive adjective to refer to a measurement for themselves. For example, a user may state, "take my blood pressure." In such an instance, that user may have been previously identified by the voice print identification performed using the voice activation command. Accordingly, identity determiner 305 may determine that the measurement is for the user account of the speaker.

A user command may also refer to an entity by name. For example, a speaker may state, "take Johnny's temperature." In such an instance, voice processor 320 may have processed the voice command to determine a name. Alternatively, the name may have been a parameter of the voice command that was received from the medical voice command device. However, many spoken names may sound similar to voice recognition systems. For example, a user may say "Hanna," but the voice recognition system may determine that the user said "Anna." Accordingly, the name determined by voice processor 320 may be treated as a candidate name. Identity determiner 305 may then compare the determined candidate name to the names of the entities for each user account associated with a voice command device. The name that most closely matches the candidate name may be determined to be the name of the stated entity, and the user account having that name may be identified as the user account to use for storing medical data associated with the voice command.

In an example, one user account associated with a voice command device may be for Hanna, another user account may be for Mark, another user account may be for Jennifer, and another user account may be for Hank. The voice processor 320 may have interpreted a voice command as naming Anna. The candidate name of Anna may be compared by identity determiner 305 to the names in each of the user accounts (e.g., to Hanna, to Mark, to Jennifer and to Hank). Based on the comparison, identity determiner 305 may determine that Hanna is the closest name to the candidate name of Anna, and so may determine that the identity of the entity associated with the measurement is Hanna.

In one embodiment, identity determiner computes, for each user account, a probability value that a candidate name matches a name associated with that user account. The user account with the highest probability value is determined to be the user account for which a measurement was taken. In one embodiment, a K nearest neighbors function is used to determine the probability values.

In one embodiment, voice command device manager 300 stores voice recordings of entity names. Each user account may include one or multiple voice recordings stating the associated entity's name. In such an implementation, identity determiner 305 may compare a received voice command to the voice recordings in each user account to identify a closest match. A user account having a voice recording that most closely matches the recitation of a name in the voice command may be identified as the user account of the entity having that name.

Identity determiner 305 may additionally use one or more heuristics to determine an identity of the entity associated with a measurement. The heuristics that are used may be based at least in part on the nature of the measurement. For example, some medical data such as a user's weight is relatively steady (e.g., changes slowly). Accordingly, if a weight measurement is received, identity determiner 305 may compare the received weight measurement to stored weight measurement values for some or all of the user accounts associated with the medical voice command device. The stored weight measurement values may be most recent weight measurement values of the user accounts. For each such weight measurement value that is compared to the received weight measurement value, a difference may be determined. In one embodiment, the user account for which the smallest difference was computed is determined to be the user account of the entity for which the weight measurement was generated. In one embodiment, a maximum difference threshold is applied to the computed weight value differences. The maximum difference threshold may be, for example, 10% of the most recent weight measurement value. If the computed difference exceeds the maximum difference threshold, then identity determiner 305 may determine that the identity of the entity for which the measurement was taken is indeterminate.

Some types of medical data/measurements are generally only collected by people who have specific health conditions. For example, a blood sugar level measurement is generally only generated for people who have diabetes. Similarly, blood pressure measurements are generally only taken by people who have high blood pressure. Accordingly, if such a measurement is received, identity determiner 305 may determine which, if any, user accounts indicate that the users associated with those user accounts have the related medical condition. Additionally, or alternatively, identity determiner may determine which, if any, user accounts have stored measurements of the same type as the received measurement. If a single user account indicates the particular medical condition and/or has stored measurements of the same type as the received measurement, then identity determiner 305 may determine that single user account as belonging to the entity for which the measurement was generated.

As discussed previously, measurements/medical data may be initiated by a medical voice command device (in which case the measurements will be associated with a voice command), or the measurements/medical data may be initiated by a medical device. If a measurement was initiated by a medical device, then there likely will not be a voice command associated with that measurement. In such an instance, only some of the above discussed techniques for determining the identity of the entity for which the measurement was generated may be applied (e.g., the heuristics that do not involve a spoken name).

In some instances identity determiner 305 may be unable to determine the identity of the entity for whom a measurement was taken. In such an instance, message generator 330 may generate an inquiry that asks a user to identify the identity of the entity. Voice command device interactor 325 may then send the inquiry to the voice command device, which may output the inquiry and receive a user's voice response. The generated inquiry may be a voice inquiry or a text inquiry. If a text inquiry is generated, then voice processor 320 may process the text inquiry to convert the text inquiry into a voice inquiry. Alternatively, the text inquiry may be sent to the medical voice command device, and the medical voice command device may convert the text inquiry into a voice inquiry before playing the voice inquiry. Voice command device interactor 325 may then receive the voice response, and voice processor 320 and identity determiner 305 may process the voice response as discussed above to determine the identity of the entity. Alternatively, the medical voice command device may process the voice response to determine an intent and/or parameters of the voice response, and may send a file including the intent and/or parameters of the voice response to voice command device manager 300.

Once an entity (e.g., a user account) associated with a measurement is determined, voice command device manager 300 stores the measurement in a medical data store 365 in an entry for that user account. The stored measurement then becomes part of a health record for the entity having that user account, and may later be accessed. The medical data store may be a database, file system, or other data storage.

After a measurement/medical data is received by voice command device manager 300, message generator 330 may process the measurement to generate a message indicating the measurement value. The message may be a voice output of the measurement, such as an audio file that, when played, outputs a voice speaking the measurement value. Alternatively, the message may be a text message that indicates the measurement value. The text message may be processed by voice processor 320 in some embodiments to convert the text message into a voice message.

Medical data analyzer 310 may analyze a received measurement/medical data 310, and may determine additional medical information associated with the measurement. For example, medical data analyzer 310 may compare the measurement to a database of measurements and/or to known healthy and unhealthy ranges of values for the measurement. Based on the comparison of the measurement to the data base of measurements, the known healthy measurements and/or the known unhealthy measurements, message generator 330 may include in the generated voice output an indication of whether the measurement is a healthy measurement or an unhealthy measurement. Message generator 330 may additionally add other information to the voice output, such as a question of whether the user wants to schedule a reminder to take a particular medication (e.g., Acetaminophen), a question of whether the user wants to schedule a doctor appointment, a question of whether the user wants to call an ambulance, and so on.

Medical data analyzer 310 may compare the measurement to one or more thresholds, and may cause message generator 330 to generate different instructions, notices and/or warnings based on whether the measurement exceeds one or more of the thresholds. For example, some temperatures may be likely to cause seizure. If a temperature measurement indicates a temperature that is likely to cause a seizure, then the message may include a recommendation to seek medical assistance right away. The thresholds to which the measurement is compared may be dependent on the entity (e.g., user account) associated with the measurement. For example, different thresholds may be applied for an infant than for a child or an adult.

A user account may include a history of measurements and/or one or more goals related to the measurements. Medical data analyzer 310 may compare the received measurement to the historical measurement data for a user account and/or to the goal(s). Medical data analyzer may then determine statistical information about the current measurement as compared to the previous measurements. Additionally, medical data analyzer 310 may determine whether the user has reached a goal and/or how far they are away from the goal. Message generator 330 may include such information in the message that is generated. Once the message is generated, voice command device interactor 325 sends the message to the voice command device (e.g., as a text message or a voice message), which then plays a voice output of the message.

Some voice commands received from users may be inquiries asking about previously received medical data of an individual. Responsive to such an inquiry, voice processor 320 may process the voice inquiry to determine the nature of the inquiry (e.g., to parse the inquiry and determine an intent and/or properties of the voice inquiry). Alternatively, intent and parameters of a voice command may be received instead of or in addition to the voice command. Identity determiner 305 may process an output of voice processor 320 (or the intent and/or voice command parameters that were received) to determine an identity of the user account associated with the inquiry. Medical data analyzer 310 may then analyze the medical data in the medical data store 365 for the indicated user to generate an answer to the inquiry. Message generator 330 then generates a message with the answer, which is sent to the voice command device by voice command device interactor 325. For example, a voice inquiry may ask "when was Johnny last sick," or "did Johnny have a fever last month," or "what weight percentile is Anna in for her age." After a particular user account for a user named Johnny is determined, medical data analyzer 310 may then analyze the medical data for that user account to determine an answer to the inquiry. For example, if the inquiry asked for when Johnny was last sick, medical data analyzer may identify a last date (e.g., Oct. 21, 2015) at which an elevated temperature was recorded for Johnny. Message generator 330 may then generate a response message stating "Johnny was last sick on Oct. 21, 2015, with a recorded temperature of X."

In one embodiment, voice command device manager 300 includes medical reminder 340. At any time, a user may issue a voice command to schedule a reminder to perform an action such as exercise, take medication, schedule a doctor appointment, and so on. Reminders may also be generated automatically based on information about a user account, such as known medical conditions of the user (e.g., diabetes), known medication prescribed to the user, known scheduled appointments of the user, and so on.

The voice command may indicate when the reminder should be issued. Alternatively, the time and/or date to issue the reminder may be determined automatically based on other information. For example, if a user is taking a prescribed medication, then the reminder may be scheduled automatically based on the prescribed frequency for taking that medication.

Medical reminder 340 may schedule an appropriate reminder for a particular date and time. If the reminder is to be repeated at a particular frequency, then a recurrent reminder may be scheduled. At the scheduled time, message generator 330 may generate a reminder, which may then be sent to the medical voice command device.

In one embodiment, voice command device manager 300 includes prescription filler 345. A doctor may prescribe medication to a user, and that prescription may be added to a user account either by the doctor's office or by the user. Prescription filler 345 may automatically contact a local pharmacy for the user and place an order for filling the prescription on the user's behalf. The local pharmacy may be indicated as a preferred pharmacy in the user account or may be determined based on a location of the user. Once the prescription is filled, the pharmacy may send a notice to the medical voice command device manager 300, and message generator 330 may generate a message stating that the prescription is ready for pickup. If a particular pharmacy does not include a medication in stock, prescription filler 345 may search for nearby pharmacies that have the medication in stock, and may place the prescription order with one of the nearby pharmacies.

In one embodiment, voice command device manager 300 includes appointment scheduler 335. Appointment scheduler 335 interfaces with doctor's offices and automates scheduling of doctor appointments for users. A user may issue a voice command to schedule a doctor appointment to the voice command device. Appointment scheduler 335 may then review a calendar of the user to determine their availability for an appointment. Appointment scheduler 335 may query the doctor's office asking for the next available appointment times. Appointment scheduler 335 may then request an earliest appointment time for which both the user and the doctor have availability, and may add that appointment to the user's calendar.

In one embodiment, voice command device manager 300 includes mobile device interactor 350. Mobile device interactor may send messages such as text reminders to a mobile device of a user in addition to, or instead of, sending voice reminders to the medical voice command device.

In one embodiment, voice command device manager 300 includes environmental safety notifier 355. Environmental safety notifier 355 determines a current location and/or predicted future location of a user and/or a location of the medical voice command device, and accesses one or more third party services to determine environmental safety information about one or more of those locations. For example, environmental safety notifier 355 may access a third party service to determine a pollen count in a location for a current day, an air pollution level for the location, any disaster warnings for the location (e.g., flood advisory, fire advisory, etc.), and so on. Voice output generator 330 may then generate a voice output that indicates the environmental safety information. Additionally, medical reminder 340 may issue a medical reminder for one or more users if the environmental safety information exceeds certain thresholds. For example, if the pollen count is above a threshold, then medical reminder 340 may issue a reminder to carry an inhaler.

In one embodiment, voice command device manager 300 includes a doctor interactor 360. A user account may include information for one or more doctors of a user. This may include information on a server computing device associated with that doctor, how to interface with the server computing device, login information for the user into the server computing device of the doctor, and so on. Alternatively, or additionally, a doctor may have his or her own account with medical data store 365, and may access a user's medical data based on a doctor-patient relationship between the user account of the doctor and the user account of the patient.

Doctor interactor 360 may perform actions such as sending medical data of a user to that user's doctor. Such actions may be performed automatically or responsive to a voice command to do so. Alternatively, or additionally, a link may be sent to the doctor (e.g., to an email address of the doctor), where the link is a link to access the medical data of the user.

Figure 4:
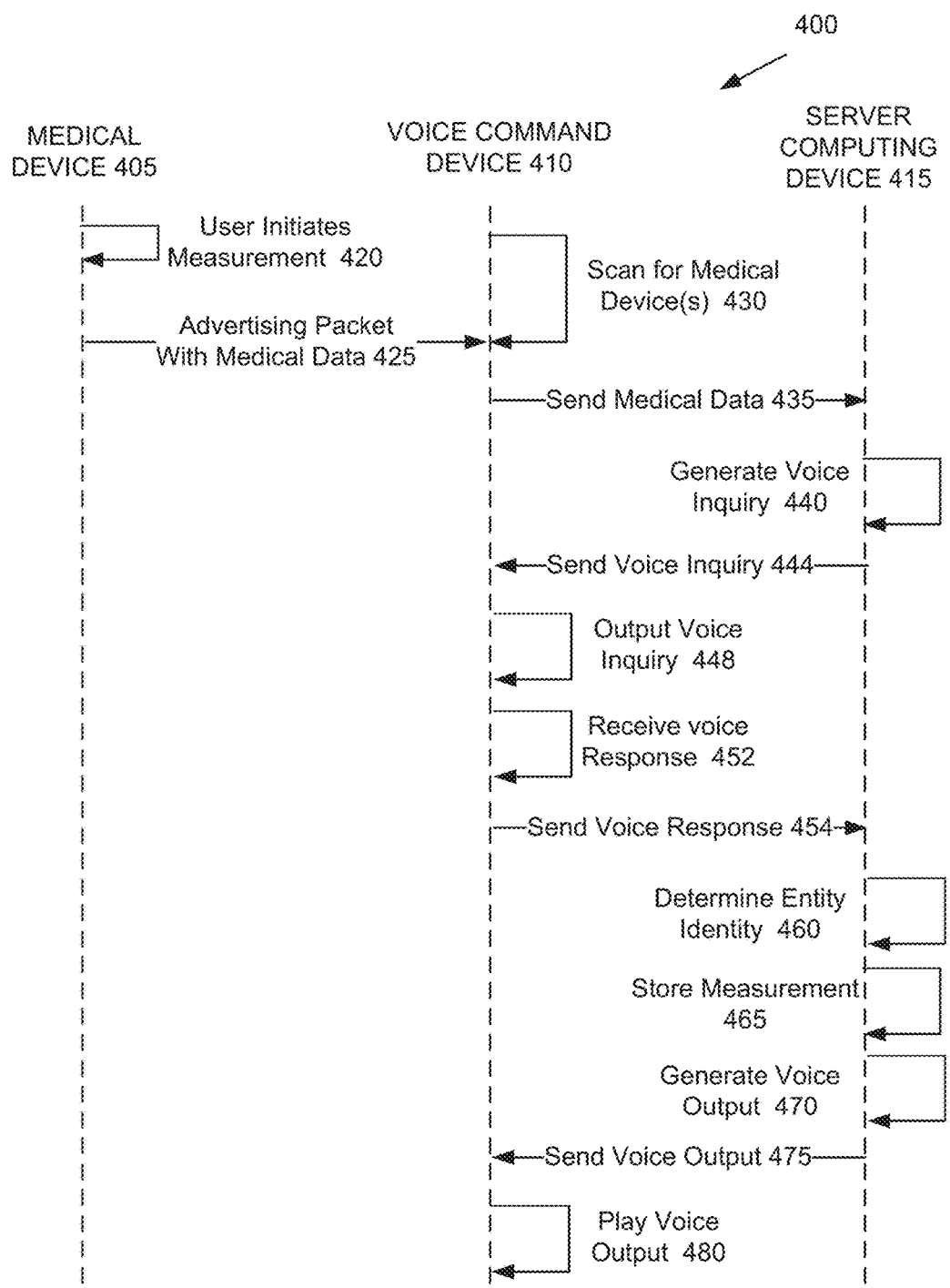
FIG. 4 is a sequence diagram illustrating one embodiment for a method of using a medical voice command device to facilitate taking a measurement for medical data.

FIG. 4 is a sequence diagram illustrating one embodiment for a method 400 of using a medical voice command device to facilitate taking a measurement for medical data. The sequence diagram begins with a user initiating a measurement 420 on a medical device 405. The medical device 405 generates the measurement and sends an advertising packet with the medical data 425 to voice command device 410. Alternatively, if the medical device 405 requires a connection to a paired device, medical device 405 may send an advertising packet to initiate a connection to voice command device 410. Once the connection is established, then medical device 405 may send the medical data in another packet or packets.

In parallel to medical device 405 sending the advertising packet 425, voice command device 410 may scan for medical devices 430, and may detect the advertising packet. Once voice command device 410 receives the medical data, voice command device 410 sends the medical data 435 to server computing device 415.

Server computing device 415 may then generate a voice inquiry 440, and may send the voice inquiry 444 to voice command device. The voice inquiry may ask for the identity of an entity for whom the measurement was taken. Alternatively, server computing device 415 may determine the identity of the entity based on information that it already possesses.

Voice command device 410 outputs (e.g., plays) the voice inquiry 448 and receives a voice response 452. Voice command device 452 sends the voice response 545 to server computing device 415. Server computing device determines the entity's identity 460, and then stores 465 the measurement in a medical data store in a user account belonging to the identified entity.

Additionally, server computing device 415 generates a voice output 470 and sends the voice output 475 to voice command device, which then plays the voice output 480.

Figure 5:
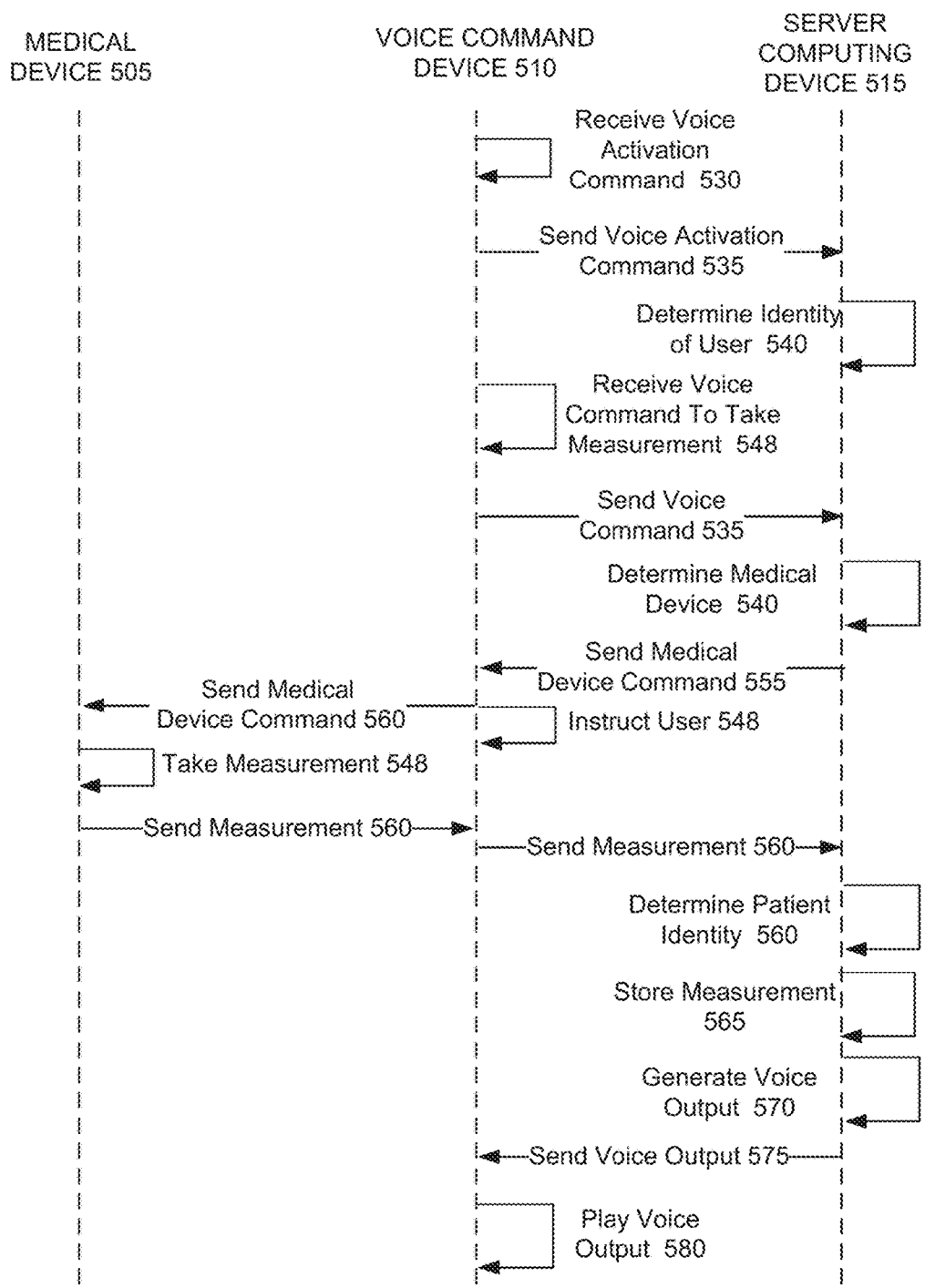
FIG. 5 is a sequence diagram illustrating one embodiment for a method of using a medical voice command device to facilitate taking a measurement for medical data.

FIG. 5 is a sequence diagram illustrating one embodiment for a method 500 of using a medical voice command device to facilitate taking a measurement for medical data. The sequence diagram begins with voice command device 510 receiving a voice activation command 530. This may cause voice command device 510 to activate. Voice command device 510 may send 535 the voice activation command to server computing device 515, which may then perform a voice print identification to identify a user 540. Alternatively, voice command device 510 may perform the voice print identification.

After activation, voice command device 510 receives a voice command to take a measurement 548. Voice command device 510 may determine a medical device to take the measurement, or may send the voice command 535 to server computing device 515, which may determine the medical device 540 to take the measurement, and may send a command to use that medical device 555 back to voice command device 510.

Once the medical device 505 to use is determined, voice command device 510 sends a command 560 to the medical device 505. In parallel, voice command device 510 may output a voice instruction 548 for the user to prepare for taking the measurement.

Medical device 505 generates the measurement 548, and then sends the measurement 560 to voice command device 510. Voice command device 510 the sends the measurement 560 to server computing device 515. Server computing device determines a patient identity (an identity of the entity for whom the measurement was taken) 560, and then stores 565 the measurement data in an appropriate user account of the determined patient/entity. Server computing device 515 generates a voice output 570 and sends the voice output 575 to voice command device, which then plays 580 the voice output.

FIGS. 6-11 are flow diagrams illustrating methods of managing medical data using a medical voice command device and associated voice command device manager running in a server computing device. These methods may be performed by processing logic that may include hardware (e.g., circuitry, dedicated logic, programmable logic, microcode, etc.), software (such as instructions run on a processing device, a general purpose computer system, or a dedicated machine), firmware, or a combination thereof. Some methods may be performed by a medical voice command device, such as medical voice command device 200 of FIG. 2. Other methods may be performed by a server computing device executing a voice command device manager, such as voice command device manager 300 of FIG. 3. Other methods may be performed partially by a medical voice command device and partially by a server computing device.

For simplicity of explanation, the methods are depicted and described as a series of acts. However, acts in accordance with this disclosure can occur in various orders and/or concurrently and with other acts not presented and described herein. Furthermore, not all illustrated acts may be performed to implement the methods in accordance with the disclosed subject matter. In addition, those skilled in the art will understand and appreciate that the methods could alternatively be represented as a series of interrelated states via a state diagram or events.

Figure 6:
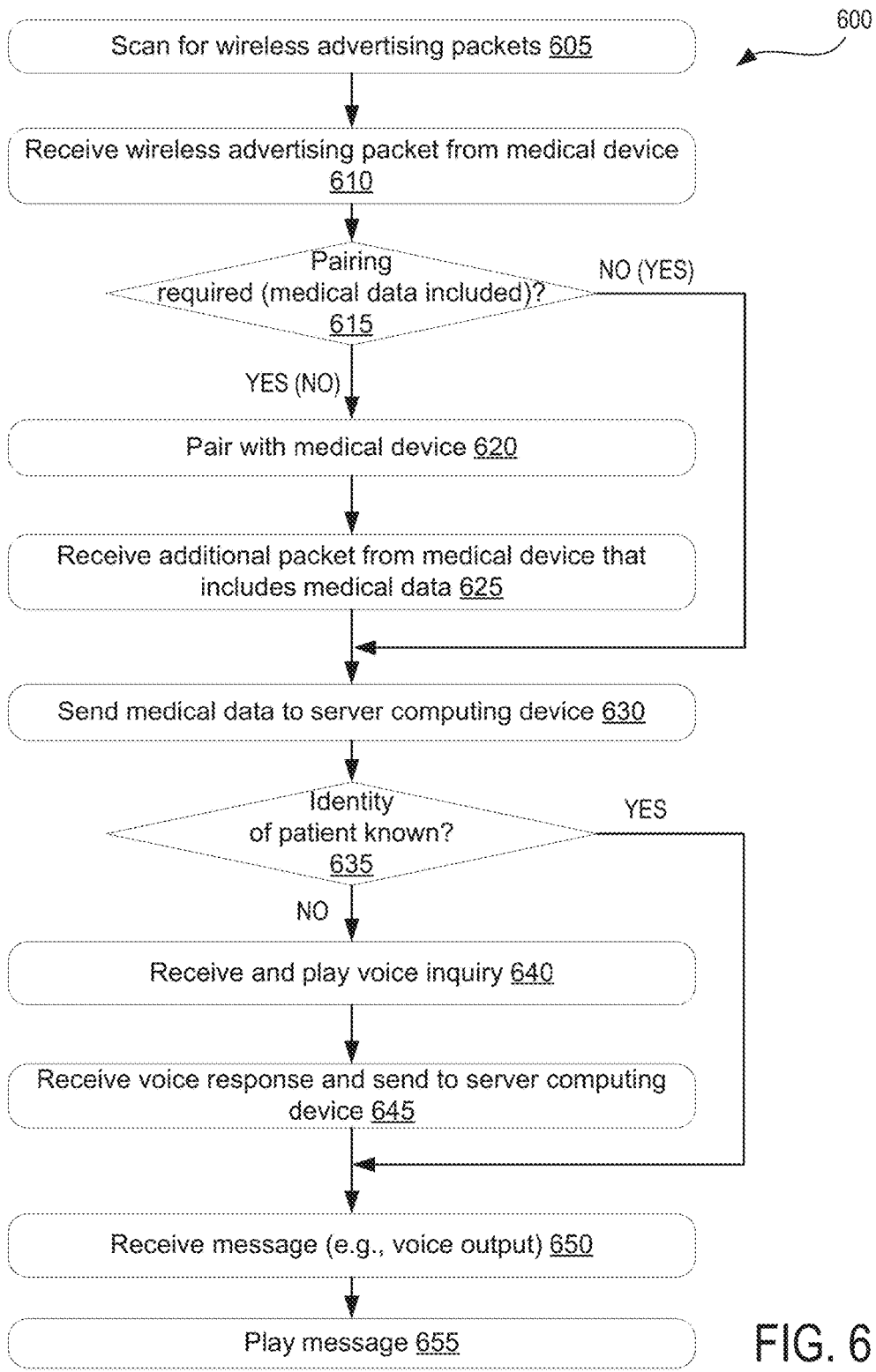
FIG. 6 is a flow diagram illustrating one embodiment for a method related to taking a measurement for medical data that is performed by a medical voice command device.

FIG. 6 is a flow diagram illustrating one embodiment for a method 600 related to taking a measurement for medical data that is performed by a medical voice command device. At block 605 of method 600, processing logic scans for wireless advertising packets. At block 610, processing logic receives an advertising packet from a medical device. At block 615, processing logic determines whether the medical device requires pairing and/or whether medical data (e.g., a measurement) was included in the advertising packet. If pairing is not required and/or medical data was included in the advertising packet, the method proceeds to block 630. If pairing is required and the advertising packet did not include medical data, the method continues to block 620.

At block 620, processing logic pairs the medical voice command device with the medical device. At block 625, the medical voice command device then receives one or more additional packet from the medical device that includes medical data.

At block 630, processing logic sends the medical data to a server computing device. At block 635, processing logic may determine whether an identity of the entity associated with the medical data is known. If the identity of the entity is known, the method proceeds block 650. Otherwise, the method continues to block 640.

At block 640, processing logic receives and plays a voice inquiry (e.g., an audio file) from the server computing device. The voice inquiry may ask for the identity of the entity. At block 645, processing logic receives a voice response via a microphone, and generates an audio file including the voice response. The audio file including the voice response may then be then sent to the server computing device at block 645. Alternatively, the voice response may be converted by processing logic into a text response, and the text response may be sent to the server computing device. Alternatively, after the voice response is converted to a text response, the text response may be processed using an intent parsing module to generate a file that includes an intent and/or parameters of the voice response. The file including the intent and/or parameters may be sent to the server computing device instead of, or in addition to, the voice response and/or the text response. At block 650, processing logic receives a message (e.g., an audio file that includes a voice output or a text file that includes a text message). Processing logic may then play that voice output at block 655, or may convert the text message into an audio message and then play the audio message.

Figure 7:
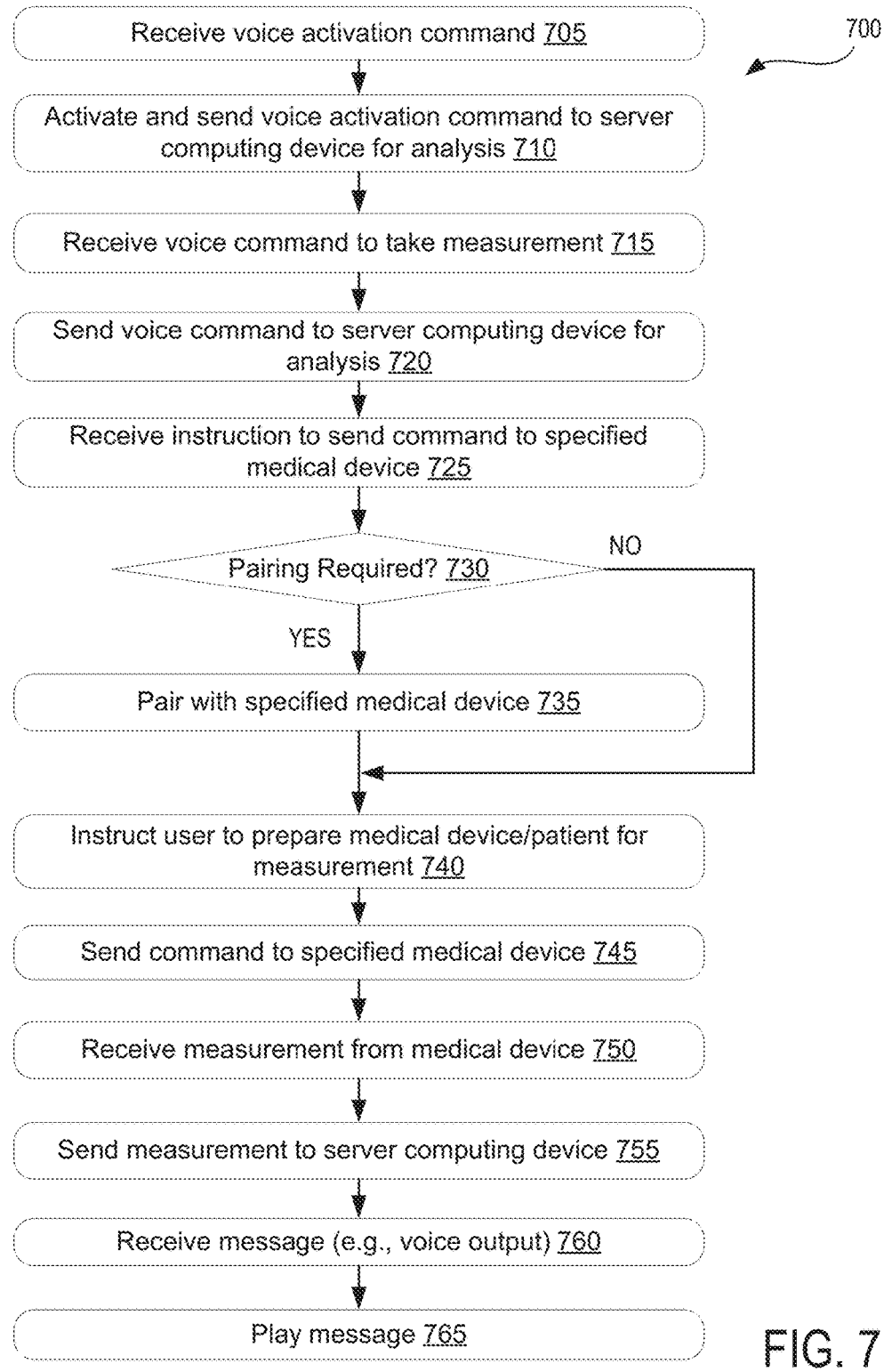
FIG. 7 is a flow diagram illustrating another embodiment for a method related to taking a measurement for medical data that is performed by a medical voice command device.

FIG. 7 is a flow diagram illustrating another embodiment for a method 700 related to taking a measurement for medical data that is performed by a medical voice command device. At block 705 of method 700, processing logic receives a voice activation command. At block 710, the medical voice command device activates and sends the voice activation command to a server computing device for analysis.

At block 715, processing logic receives a voice command to take a measurement. The voice command may be received via a microphone. An audio file of the voice command may be generated. In one embodiment, at block 720, processing logic sends the voice command (e.g., the audio file including the voice command) to the server computing device for analysis. Processing logic may then receive an instruction from the server computing device to send a command to a specified medical device to initiate the measurement. Alternatively, processing logic may perform one or more operations to convert the voice command to a text command and then to determine an intent and/or properties of the text command. This may enable processing logic to determine a medical device to send a command to for initiating a measurement without consulting with the server computing device (e.g., without sending the voice command to the server computing device or receiving a response).

At block 730, processing logic determines whether the medical device requires pairing. If pairing is not required, the method proceeds to block 740. If pairing is, the method continues to block 735. At block 735, processing logic pairs the medical voice command device with the medical device.

At block 740, the medical voice command device outputs an instruction for a user to prepare the medical device and/or a patient for taking the measurement. At block 745, processing logic sends a command to the specified or determined medical device. At block 750, processing logic receives a measurement from the medical device. At block 755, processing logic sends the measurement to the server computing device. At block 760, processing logic receives a message. Processing logic may then play a voice output of the message at block 765.

Figure 8:
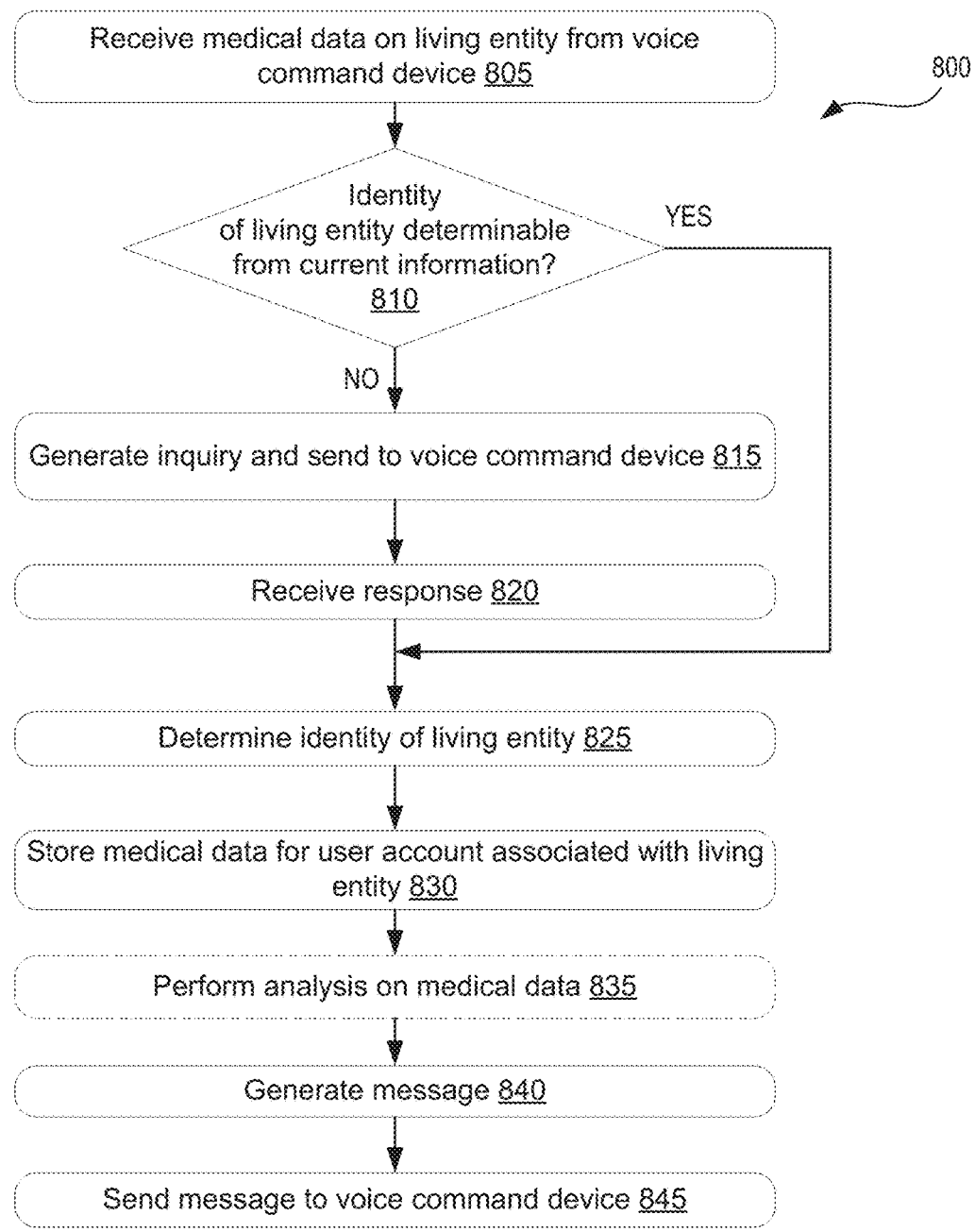
FIG. 8 is a flow diagram illustrating one embodiment for a method of acting on medical data from a voice command device.

FIG. 8 is a flow diagram illustrating one embodiment for a method 800 of acting on medical data from a voice command device. Method 800 may be performed by a server computing device executing a voice command device manager. At block 805 of method 800, processing logic receives medical data (e.g., a measurement) on a living entity from a voice command device. At block 810, processing logic determines whether an identity of the living entity is determinable using current information (e.g., the medical data, known user accounts associated with the voice command device, historical medical data for those known user accounts, an identity of a last user who activated the medical voice command device, and so on). If the current information is sufficient to determine an identity of the entity, the method continues to block 820. Otherwise the method continues to block 815.

At block 815, processing logic generates an inquiry and sends the inquiry to the voice command device. The inquiry may be a voice inquiry in the form of an audio file that asks the identity of the entity that may be played by the voice command device. Alternatively, the inquiry may be a text inquiry that will be converted to a voice inquiry by the medical voice command device. At block 820, processing logic receives a response. The response may be a voice response received as another audio file (e.g., an MP3 file, a WAV file, an AAC file, or other audio file). Alternatively, the response may be a text response. Alternatively, the response may be a file such as a JSON file that includes an intent of the voice response and/or properties of the voice response.

At block 825, processing logic determines an identity of the living entity using the voice response and/or the other information on hand. At block 830, processing logic stores the medical data in a user account associated with the identified living entity.

At block 835, processing logic may perform an analysis on the medical data, as described above. At block 840, processing logic may generate a message, which may be a voice output (e.g., another audio file) or a text message. The message may include a result of the analysis if the analysis was performed at block 835. At block 845, processing logic sends the message to the voice command device for playback.

Figure 9:
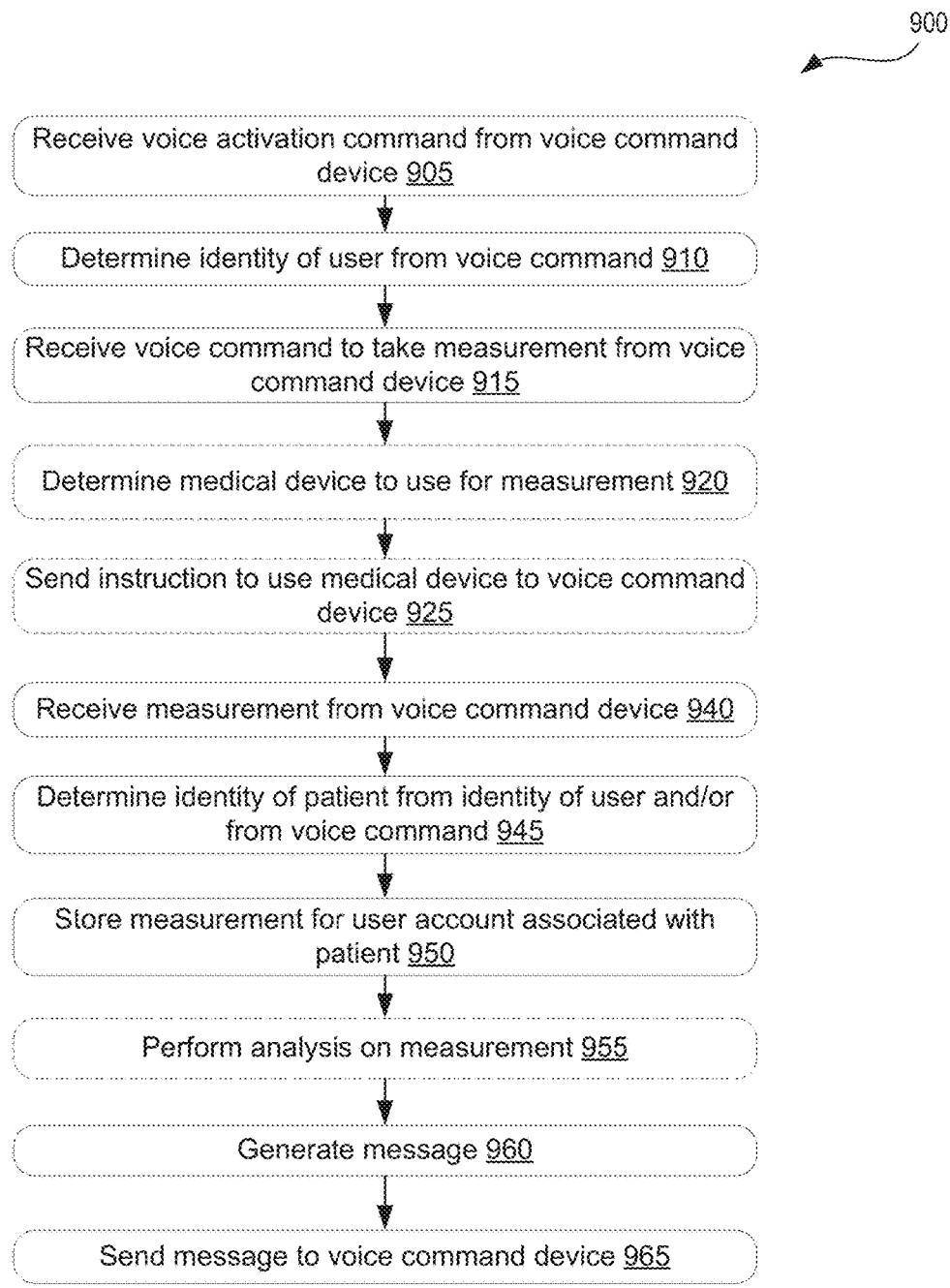
FIG. 9 is a flow diagram illustrating another embodiment for a method of acting on medical data from a voice command device.

FIG. 9 is a flow diagram illustrating another embodiment for a method 900 of acting on medical data from a voice command device. Method 900 may be performed by a server computing device executing a voice command device manager. At block 905 of method 900, processing logic receives a voice activation command from a voice command device. The voice activation command may be received as an audio file that was recorded by the voice command device. At block 910, processing logic determines an identity of a user from the voice command (e.g., by performing voice print identification).

At block 915, processing logic receives a voice command from the voice command device. The voice command may be received as another audio file that was generated by the voice command device. At block 920, processing logic may determine a medical device to use for taking the measurement. At block 925, processing logic may send in instruction to use the determined medical device to the voice command device. Alternatively, the voice command device may determine which medical device to use without the assistance of the server computing device (in which case the operations of block 920 and 925 may not be performed).

At block 940, processing logic receives a measurement from the voice command device. AT block 945, processing logic determines an identity of a patient (an entity for whom the measurement was taken) based on the identity of the user and/or based on contents of the voice command. This determination may be performed as described in detail above. At block 950, processing logic stores the measurement for the user account associated with the determined patient.

At block 955, processing logic may perform an analysis on the medical data, as described above. At block 960, processing logic may generate a message. The message may include a result of the analysis if the analysis was performed at block 955. At block 965, processing logic sends the message to the voice command device.

Figure 10:
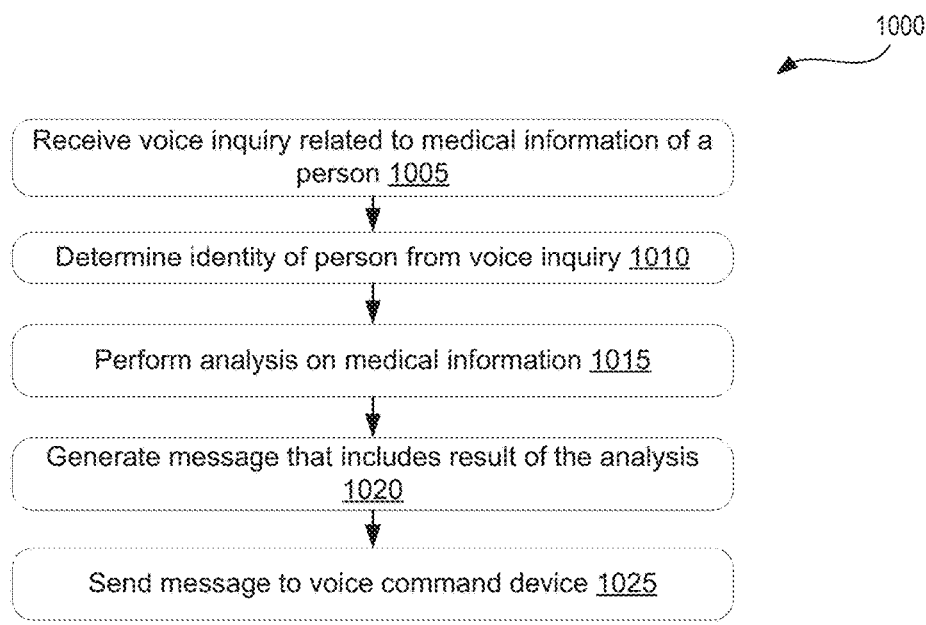
FIG. 10 is a flow diagram illustrating an embodiment for a method of responding to a health related voice inquiry from a voice command device.

FIG. 10 is a flow diagram illustrating an embodiment for a method 1000 of responding to a health related voice inquiry from a voice command device. Method 1000 may be performed by a server computing device. At block 1005 of method 1000, processing logic receives a voice inquiry related to medical information of a person. The voice inquiry may be received as an audio file from a medical voice command device. At block 1010, processing logic determines an identity of the person from the voice inquiry. At block 1015, processing logic determines an analysis on the medical information for the determined person. The medical data may be stored in a medical data store in a user account for that person. At block 1020, processing logic generates a message that includes a result of the analysis. The message may be another audio file. At block 1025, processing logic sends the message to the voice command device.

Figure 11:
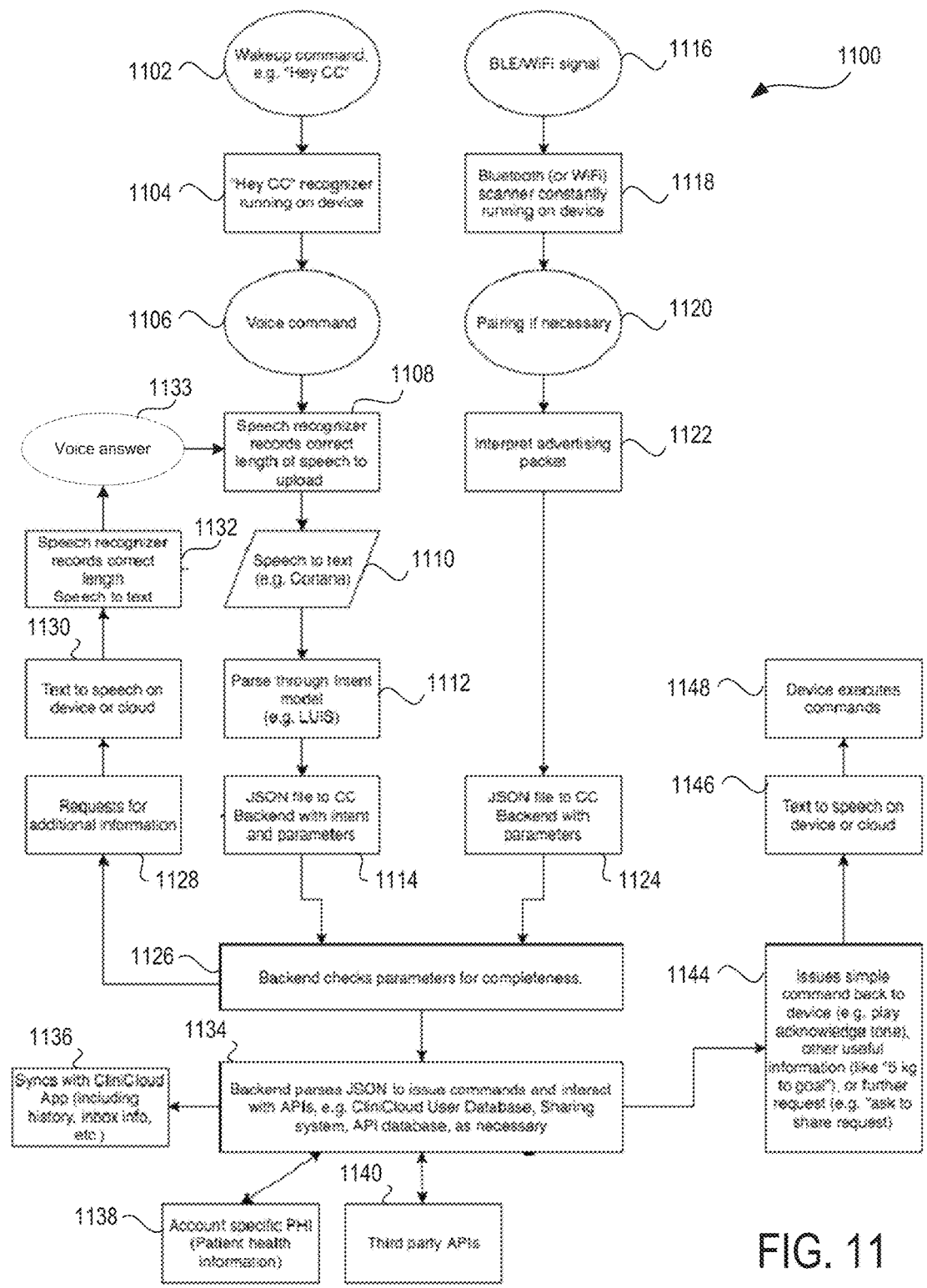
FIG. 11 is a flow diagram illustrating an embodiment for a method of managing medical data by a medical voice command device and an associated backend server that interfaces with the medical voice command device.

FIG. 11 is a flow diagram illustrating an embodiment for a method 1100 of managing medical data by a medical voice command device and an associated backend server that interfaces with the medical voice command device. Method 1100 may begin at block 1102 or at block 1116.

At block 1102, a wakeup command is received by a medical voice command device. At block 1104, a wakeup command recognizer of the medical voice command device processes the wakeup command, determines that it satisfies the criteria for a wakeup command, and activates the medical voice command device. At block 1106, a voice command is received by the now active medical voice command device. At block 1108, a speech recognizer of the medical voice command device determines a length of the voice command and records the voice command having the determined length into an audio file. The speech recognizer may correspond to voice interface 264 of FIG. 2 in an embodiment.

At block 1110, the medical voice command device processes the voice command by performing voice recognition to generate a text output from the audio of the voice command. In one embodiment, the medical voice command device uses a third party speech processing service such as Cortana for the speech recognition and speech to text operations. This may include sending the audio file to a remote server that provides the third party service. Alternatively, the medical voice command device may send the voice command audio file to a server computing device executing a voice command device manager, which may include a voice processor.

At block 1112, the medical voice command device parses the text through an intent model (e.g., Microsoft's LUIS). The intent model may include a list of supported operations and voice commands that can initiate those operations. The text may be compared to each of the supported voice commands for a possible match. A match may be determined based on a similarity value and/or probability of match value that may be generated as a result of the comparisons.

At block 1114, the medical voice command device generates a file with the identified intent (e.g., the identified operation associated with the voice command). The file may additionally include parameters associated with the operation, such as a type of measurement to make, a type of inquiry, a medical device to generate the measurement, and so on. The file is a JSON file in one embodiment.

At block 1126, the server computing device checks the parameters of the received file for completeness. If the voice command was missing one or more parameters, then the method proceeds to block 1128, at which a request for additional information is sent to the medical voice command device. The server computing device or the medical voice command device may perform text to speech to generate an audio request for the additional information. At block 1132, a speech recognizer running on the medical voice command device or the server computing device may record a correct length of the speech from the text. The voice request may then be sent to the medical voice command device, which may receive a voice response from a user at block 1133. The voice response may be processed by the speech recognizer at block 1108.

If at block 1126 the parameters for a particular operation are complete, the method proceeds to block 1134. At block 1134, the server computing device (backend) parses the file (e.g., the JSON file) to issue commands and interact with one or more application programming interfaces (APIs), such as an API for a medical data store and/or one or more third party APIs.

The subsequent operations performed by the server computing device may vary depending on the requested operation. At block 1136, the server computing device may synchronize with an application executing on a mobile device of a user (e.g., by adding received measurement data to the application). At block 1138, the server computing device may access and/or add data (e.g., patient health information such as a measurement or other medical data) to a user account. At block 1140, the server computing device may interface with one or more third party APIs.

At block 1144, the server computing device may issue a simple command back to the medical voice command device. The command may be a command to play an acknowledge tone, a command to play a voice output of text provided by the server computing device, a command to play a voice inquiry of text provided by the server computing device, and so on. At block 1146, the server computing device or the medical voice command device may perform text to speech to generate an audio output of the voice output or voice inquiry. At block 1148, the medical voice command device executes the commands, which may include playing received audio files including a voice output and/or voice inquiry.

Method 1100 may alternatively begin at block 1116, at which the medical voice command device receives an unsolicited wireless message such as a BLE advertising packet or a Wi-Fi signal. At block 1118, the medical voice command device scans for and intercepts the unsolicited wireless message. At block 1120, the medical voice command device pairs with the medical device is necessary. AT block 1122, the medical voice command device interprets the received unsolicited wireless message (e.g., an advertising packet that may include measurement data). At block 1124, the medical voice command device may generate a file including parameters such as the measurement, a medical device that the measurement was received from, and so on. The file may be a JSON file in one embodiment. The medical voice command device then sends the file to the server computing device (backend). The method may then proceeds from block 1126 as described above.

Figure 12:
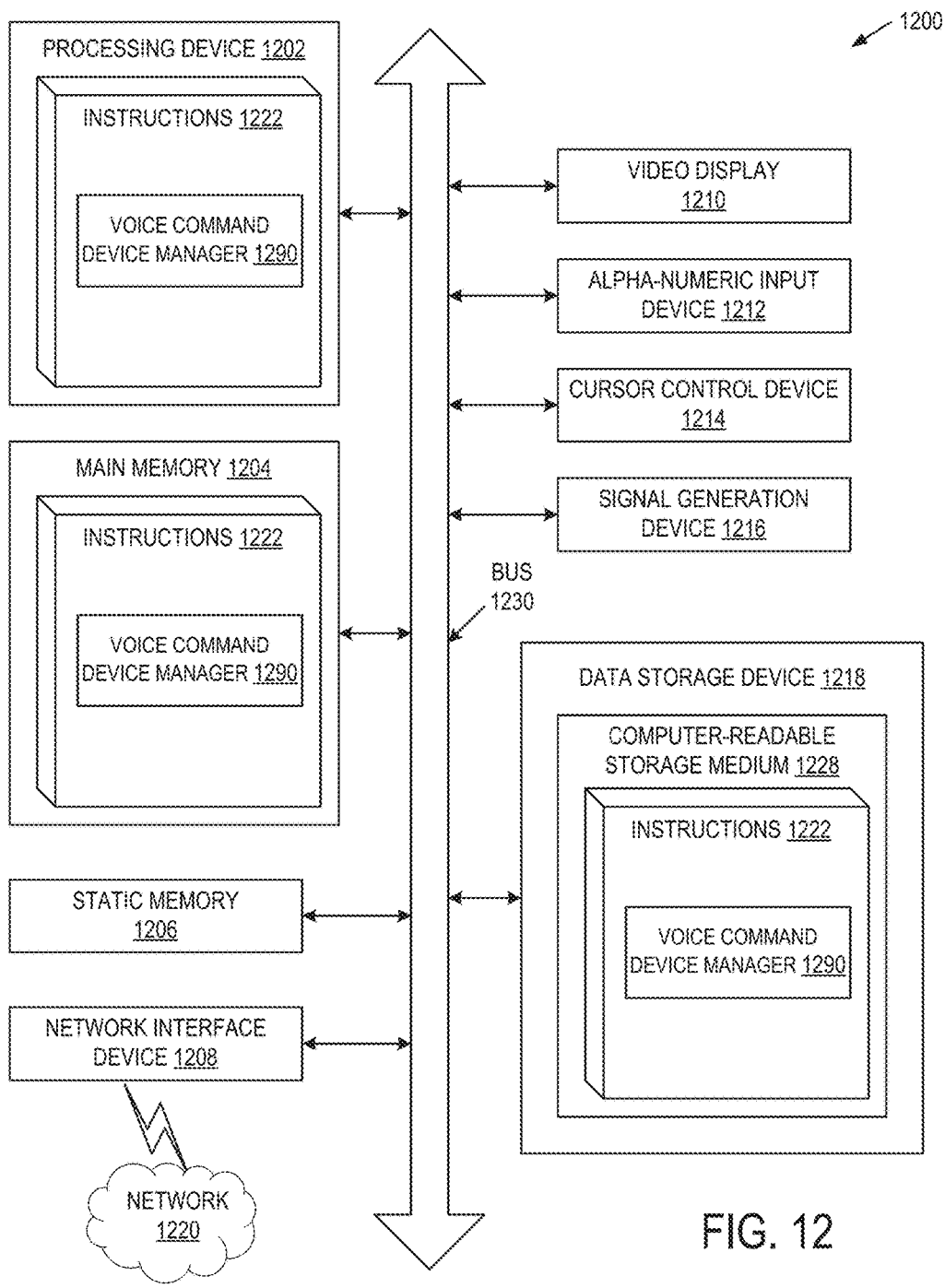
FIG. 12 illustrates an example computing device, in accordance with one embodiment.

FIG. 12 illustrates a diagrammatic representation of a machine in the example form of a computing device 1200 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a secondary memory (e.g., a data storage device 1218), which communicate with each other via a bus 1230.

Processing device 1202 represents one or more general-purpose processors such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. Processing device 1202 is configured to execute the processing logic (instructions 1222) for performing the operations and steps discussed herein.

The computing device 1200 may further include a network interface device 1208. The computing device 1200 also may include a video display 1210 (e.g., a liquid crystal display (LCD) or a cathode ray tube (CRT)), an alphanumeric input device 1212 (e.g., a keyboard), a cursor control device 1214 (e.g., a mouse), and/or a signal generation device 1216 (e.g., a speaker).

The data storage device 1218 may include a machine-readable storage medium (or more specifically a computer-readable storage medium) 1228 on which is stored one or more sets of instructions 1222 embodying any one or more of the methodologies or functions described herein. The instructions 1222 may also reside, completely or at least partially, within the main memory 1204 and/or within the processing device 1202 during execution thereof by the computer system 1200, the main memory 1204 and the processing device 1202 also constituting computer-readable storage media.

The computer-readable storage medium 1228 may also be used to store voice command device manager 1290 (as described with reference to the preceding figures), and/or a software library containing methods that call an access control manager 1290. While the computer-readable storage medium 1228 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium that is capable of storing or encoding a set of instructions for execution by the machine and that cause the machine to perform any one or more of the methodologies described herein. The term "non-transitory computer-readable storage medium" shall accordingly be taken to include, but not be limited to, solid-state memories, and optical and magnetic media.

The modules, components and other features described herein (for example in relation to FIG. 3) can be implemented as discrete hardware components or integrated in the functionality of hardware components such as ASICS, FPGAs, DSPs or similar devices. In addition, the modules can be implemented as firmware or functional circuitry within hardware devices. Further, the modules can be implemented in any combination of hardware devices and software components, or only in software.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "scanning", "detecting", "determining", "storing", "initiating", or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the discussed purposes, or it may comprise a general purpose computer system selectively programmed by a computer program stored in the computer system. Such a computer program may be stored in a computer readable storage medium, such as, but not limited to, any type of disk including floppy disks, optical disks, CD-ROMs, and magnetic-optical disks, read-only memories (ROMs), random access memories (RAMs), erasable programmable read only memories (EPROMs), electrically erasable programmable read only memories (EEPROMs), magnetic disk storage media, optical storage media, flash memory devices, other type of machine-accessible storage media, or any type of media suitable for storing electronic instructions, each coupled to a computer system bus.

It is to be understood that the above description is intended to be illustrative, and not restrictive. Many other embodiments will be apparent to those of skill in the art upon reading and understanding the above description. Although the present invention has been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A voice command device comprising:
   a speaker;
   a microphone;
   a wireless communication module; and
   a processing device operatively coupled to the speaker, to the microphone, and to the wireless communication module, the processing device to:
   receive, via the microphone from a user, a voice command to generate a measurement comprising medical data of a patient, the patient being a living entity;
   determine a medical device that is to generate the measurement;
   send, via the wireless communication module, a command to the medical device to cause the medical device to generate the measurement;
   receive, via the wireless communication module, the measurement from the medical device; and
   send the measurement to a server computing device, wherein:
   the server computing device is to:
      maintain a relationship data structure identifying one or more relationships among a plurality of user accounts associated with the voice command device,
      determine, based on content of the voice command to generate the measurement comprising the medical data of the patient, a relationship between the patient and the user
      compare the relationship between the patient and the user to the one or more relationships in the relationship data structure,
      determine a user account of the patient from the plurality of user accounts associated with the voice command device based on the comparison, and
      store the measurement in the user account of the patient.

2. The voice command device of claim 1, wherein the processing device is further to:
   output, via the speaker, a voice response instructing a user to prepare the medical device for generation of the measurement prior to receiving the medical data.

3. The voice command device of claim 1, wherein the server computing device is to determine an identity of the patient and generate a message associated with the measurement, and wherein the processing device is to:
   receive the message from the server computing device; and
   output the message via the speaker.

4. The voice command device of claim 1, wherein to determine the medical device that is to generate the measurement the processing device is to:
   initiate transcription of the voice command to generate a text version of the voice command;
   parse the text version of the voice command using an intent model to determine a type of measurement to be generated; and
   determine a medical device associated with the voice command device that is capable of generating the type of measurement.

5. A method comprising:
   receiving, by a processing device, at least one of a) a voice command of a user or b) parameters of the voice command from a voice command device, wherein the voice command is a command to generate a measurement comprising medical data of a patient, the patient being a living entity;
   receiving, by the processing device, medical data of the patient in association with the voice command;
   maintaining a relationship data structure identifying one or more relationships among a plurality of user accounts associated with the voice command device;
   determining, based on at least one of content of the voice command to generate the measurement comprising the medical data of the patient or the parameters of the voice command to generate the measurement comprising the medical data of the patient, a relationship between the patient and the user;
   comparing the relationship between the patient and the user to the one or more relationships in the relationship data structure;
   determining a user account of the patient from the plurality of user accounts associated with the voice command device based on the comparison;
   storing the medical data in the user account of the patient;
   generating a message associated with the medical data; and
   sending the message to the voice command device.

6. The method of claim 5, further comprising:
   receiving a voice activation command of the user from the voice command device prior to receiving the voice command; and
   performing voice print identification using the voice activation command to identify the user.

7. The method of claim 6, wherein the voice command uses a possessive pronoun or a possessive adjective to identify the patient, the method further comprising:
   determining a first entry in the relationship data structure that corresponds to the user based on an identity of the user; and
   determining a second entry in the relationship data structure based on the possessive pronoun or the possessive adjective in the voice command, wherein the second entry indicates an identity of the patient.

8. The method of claim 6, wherein the voice command uses a possessive pronoun or a possessive adjective to identify the patient, the method further comprising:
   determining that the possessive pronoun or the possessive adjective identifies the user as the patient.

9. The method of claim 5, wherein the voice command identifies the patient by name, and wherein one of the parameters of the voice command is a candidate name determined based on performing voice recognition on the voice command, the method further comprising:
   comparing the candidate name to a list of names associated with the voice command device;
   determining a name from the list of names that most closely matches the candidate name; and
   determining that the patient corresponds to the name from the list of names that most closely matches the candidate name.

10. The method of claim 9, wherein determining the name that most closely matches the candidate name comprises:
   determining a match probability for each name in the list of names; and
   selecting the name from the list of names that has a highest match probability as the name that most closely matches the candidate name.

11. The method of claim 5, further comprising:
receiving, from the voice command device, at least one of a voice inquiry related to additional medical data or parameters of the voice inquiry;
performing an analysis of the additional medical data;
generating a response to the voice inquiry, the response comprising a result of the analysis; and
sending the response to the voice command device.

12. A method comprising:
receiving a voice command of a user from a voice command device, wherein the voice command is a command to generate a measurement comprising medical data of a patient;
receiving, by a processing device, medical data of the patient from the voice command device, the medical data having been generated by a medical device and sent to the voice command device;
maintaining a relationship data structure identifying one or more relationships among a plurality of user accounts associated with the voice command device;
determining, based on at least one of content of the voice command to generate the measurement comprising the medical data of the patient or parameters of the voice command to generate the measurement comprising the medical data of the patient, a relationship between the patient and the user;
comparing the relationship between the patient and the user to the one or more relationships in the relationship data structure;
determining a user account of the patient from a plurality of user accounts associated with the voice command device based on the comparison;
storing the medical data in the user account associated with the patient;
generating a message associated with the medical data; and
sending the message to the voice command device.

13. The method of claim 12, the method further comprising:
generating an inquiry that asks for an identity of the patient;
sending the inquiry to the voice command device;
receiving at least one of a voice answer or parameters of the voice answer indicating the identity of the patient; and
determining the identity of the patient from at least one of the voice answer or the parameters of the voice answer.

14. The method of claim 13, wherein the voice answer identifies the patient by name, and wherein one of the parameters of the voice answer is a candidate name determined based on performing voice recognition on the voice answer, the method further comprising:
comparing the candidate name to a list of names associated with the voice command device;
determining a name from the list of names that most closely matches the candidate name; and
determining that the patient corresponds to the name from the list of names that most closely matches the candidate name.

15. The method of claim 12, the method further comprising:
comparing the medical data to stored medical data of the plurality of user accounts, wherein each of the plurality of user accounts is associated with a different patient;
determining stored medical data that most closely matches the medical data; and
determining a particular user account of the plurality of user accounts that comprises the stored medical data that most closely matches the medical data.

* * * * *